United States Patent [19]

Katsuragi et al.

[11] 4,400,316
[45] Aug. 23, 1983

[54] C-TERMINAL FRAGMENT OF HUMAN CHORIONIC GONADOTROPIN

[75] Inventors: Shigeo Katsuragi; Kaoru Morita, both of Shizuoka; Sadami Kobari, Mishima; Toshiharu Noda, Shizuoka; Nobuaki Nakagawa, Shizuoka; Susumu Watanabe, Shizuoka, all of Japan

[73] Assignee: Toyo Jozo Kabushiki Kaisha, Shizuoka, Japan

[21] Appl. No.: 320,699

[22] Filed: Nov. 12, 1981

[30] Foreign Application Priority Data

Nov. 11, 1980 [JP] Japan .................................. 55-158567

[51] Int. Cl.$^3$ ........................................... C07C 103/52
[52] U.S. Cl. ............................................. 260/112.5 R
[58] Field of Search ................................. 260/112.5 R

[56] References Cited

PUBLICATIONS

Kawaski et al., Chem. Pharm. Bull. 28(9) 2692–2698, 2699–2706 (1980).

Primary Examiner—Delbert R. Phillips
Assistant Examiner—F. T. Moezie
Attorney, Agent, or Firm—Young & Thompson

[57] ABSTRACT

A peptide of the formula

R-SER-LEU-PRO-SER-PRO-SER-ARG-LEU-
PRO-GLY-PRO-SER-ASP-THR-PRO-ILE-
LEU-PRO-GLN-OH wherein
R: H or $R_1$-Ser-Ser-Ser-Ser-Lys-Ala-Pro-Pro-Pro group,
$R_1$: H or $R_2$-$R_3$-Asp-Asp-Pro-Arg-Phe-Gln-Asp group,
$R_2$: H or $R_4$-Asp-His-Pro-Leu-Thr group,
$R_4$: H-$R_5$-Gly-Gly-Pro-Lys group,
$R_5$: Cys or Tyr group, and
$R_3$: Cys or S-acetamidemethyl-Cys group, or salt thereof, has utility for the preparation of antibodies for assaying human chorionic gonadotropin or as a labelling reagent.

1 Claim, No Drawings

C-TERMINAL FRAGMENT OF HUMAN CHORIONIC GONADOTROPIN

This invention relates to the C-terminal of human chorionic gonadotropin (HCG). More particularly the present invention relates to a peptide of the formula

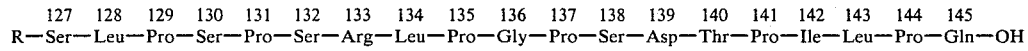

wherein
- R: H or $R_1$-Ser-Ser-Ser-Ser-Lys-Ala-Pro-Pro-Pro group,
- $R_1$: H or $R_2$-$R_3$-Asp-Asp-Pro-Arg-Phe-Gln-Asp group,
- $R_2$: H or $R_4$-Asp-His-Pro-Leu-Thr group,
- $R_4$: H-$R_5$-Gly-Gly-Pro-Lys group,
- $R_5$: Cys or Tyr group, and
- $R_3$: Cys or S-acetamidemethyl-Cys group, or a salt thereof.

HCG is a glycoprotein hormone secreted from placenta at pregnancy, and has an important role for maintaining pregnancy. Quantitative or qualitative analysis of HCG can be used for the diagnosis of pregnancy, ectopic pregnancy or choriocarcinoma. However, there are a luteinizing hormone (LH), a follicle-stimulating hormone (FSH) and a chorionic gonadotropin (CG) in the gonadotropic hormone, and their molecular structures resemble each other, and these are glycoproteins. Moreover, they consist of two sub-units of α- and β-chain. Exchange of the α-chain in each gonadotropic hormone does not affect their activity, and hence the structures of the α-chains closely resemble in each other. The β-chain is specific for each gonadotropin, but the β-chains of LH and CG are quite similar. However, the amino acid sequence adjacent the C-terminal of the β-chain of CG can be differentiated; therefore, an accurate and reliable CG assaying system can be provided without confusion with the other gonadotropic hormones, especially LH.

The present invention makes use of this concept, and the antibody obtained from the antigen consisting of the novel peptide of formula [I] has immune crossing activity. The peptide [I] is thus useful for the preparation of an antibody for assaying HCG or a labelling reagent.

The synthesis of peptide [I] of the present invention can be carried out as follows:

An amino acid and/or lower peptide is reacted by condensation in the order of the amino acid sequence of formula [I], and the protective group for the reactive group is released at the final stage of the reaction. The condensation reaction can be carried out by conventional peptide synthesis by repeating the attaching and removal of the protective groups and condensation. The protective groups for the synthesis of the starting materials or intermediates are conventional protective groups for peptide synthesis and are easily removable by hydrolysis, acid decomposition, reduction, aminolysis or hydrazinolysis.

For example, the amino group may be protected conventionally by an acyl group such as formyl, trifluoroacetyl, phthaloyl, benzenesulfonyl, p-toluenesulfonyl, o-nitrophenylsulfonyl or 2,4-dinitrophenylsulfonyl group; an aralkyl group such as benzyl, diphenylmethyl or triphenylmethyl (these groups may optionally be substituted with a lower alkoxy group such as o-methoxy or p-methoxy); a benzyloxycarbonyl group such as benzyloxycarbonyl, o-bromobenzyloxycarbonyl, p-bromobenzyloxycarbonyl, o-chlorobenzyloxycarbonyl, p-nitrobenzyloxycarbonyl, p-methoxybenzyloxycarbonyl, p-phenylazobenzyloxycarbonyl or p-(p'-methoxyphenylazo)-benzyloxycarbonyl; an aliphatic oxycarbonyl group such as cyclopentyloxycarbonyl, trichloroethyloxycarbonyl, t-amyloxycarbonyl, t-butoxycarbonyl or diisopropylmethoxycarbonyl, or an aralkyloxycarbonyl group such as 2-phenylisopropoxycarbonyl, 2-tolylisopropoxycarbonyl or 2-p-diphenyl-isopropoxycarbonyl. These amino groups can be protected by forming enamin reacted with 1,3-diketone such as benzolyacetone, acetylacetone or dimedone.

The carboxyl group can be protected by amide formation, hydrazide formation or esterification. The amide group is substituted with a 3,4-dimethoxybenzyl or bis-(p-methoxy-phenyl)-methyl group. The hydrazide group is substituted with a benzyloxycarbonyl, trichloroethyloxycarbonyl, trifluoroacetyl, t-butoxycarbonyl, trityl or 2-p-diphenyl-isopropoxycarbonyl group. The ester group is substituted with an alkanol such as methanol, ethanol, t-butanol or cyanomethylalcohol; an aralkanol such as benzylalcohol, p-bromobenzylalcohol, p-chlorobenzylalcohol, p-methoxybenzylalcohol, p-nitrobenzylalcohol, 2,4,6-trimethylbenzylalcohol, benzhydrylalcohol, benzoylmethylalcohol, p-bromobenzoylmethylalcohol or p-chlorobenzoylmethylalcohol; a phenol such as 2,4,6-trichlorophenyl, 2,4,6-trichlorophenol, pentachlorophenol, p-nitrophenol, 2,4-dinitrophenol, p-cyanophenol or p-methanesulfonylphenol; or a thiophenol such as thiophenol, thiocresol or p-nitrothiophenol. The hydroxy group is serine, threonine or tyrosine may optionally be protected by esterification or etherification. A group protected by esterification is, for example, a lower alkanoyl group such as an acetyl group; an aroyl group such as a benzoyl group; or a group derived from carbonyl such as benzyloxycarbonyl or ethyloxycarbonyl. A group protected by etherification is, for example, a benzyl, tetrahydropyranyl or t-butyl group. Protection of the hydroxy group can be effected by a 2,2,2-trifluoro-1-t-butyloxycarbonylaminoethyl or 2,2,2-trifluoro-1-benzyloxycarbonylaminoethyl group. However it is not always necessary to protect these hydroxy groups.

The amino group in the guanidino group in arginine can be protected by a nitro, tosyl or benzyloxycarbonyl group. However it is not always necessary to protect the guanidino group.

The imino group in histidine can be protected by a benzyl, trityl, benzyloxycarbonyl, tosyl, adamantyloxycarbonyl, 2,2,2-trifluoro-1-t-butyloxycarbonylaminoethyl or 2,2,2-trifluoro-1-benzyloxycarbonylaminoethyl group, although the imino group does not always require to be protected.

The mercapto group is cysteine can be protected by a benzyl, p-methoxybenzyl, p-nitrobenzyl, trityl, benzylthiomethyl, ethylcarbamoyl or acetamidemethyl group.

The peptide [I] is synthesized by the condensation of amino acids of lower peptides. For example, an amino acid or peptide having a protected α-amino group and an activated terminal carboxyl group is reacted with an amino acid or peptide having a free α-amino group and protected terminal carboxyl group. On the other hand, an amino acid or peptide having an activated α-amino group and protected terminal carboxyl group is reacted with amino acid or peptide having a free terminal carboxyl group and a protected α-amino group.

The carboxyl group can be activated by, for example, an acid azide, acid anhydride, acid imidazolide or active ester, such as by converting to cyanomethyl ester, thiophenylester, p-nitrophenylester, p-nitrothiophenylester, p-methanesulfonylphenylester, thiodylester, 2,4-dinitrophenylester, 2,4,5-trichlorophenylester, 2,4,6-trichlorophenylester, pentachlorophenylester, N-hydroxysuccinimide ester, N-hydroxyphthalimido ester, 8-hydroxyquinoline ester or N-hydroxypiperidine ester, carbodiimide, N,N'-carbonyldiimidazol or an isoxazolium salt such as Woodward reagent.

The preferred condensation reactions are the carbodiimide, azide, active ester and acid anhydride methods. In the condensation reaction, racemization should carefully be avoided, and the preferred methods are the azide, active ester method, Wünsch method [Z. Naturforsch., 216, 426 (1966)] or Geiger method [Chem. Ber., 103, 788 (1970)], especially using N-ethyl-N'-3-dimethylaminopropyl-carbodiimide (WSCI) as a condensation agent.

The process of the present invention is preceded by a condensation reaction in the amino acid sequence of the formula [I], and it is preferable to synthesize from the C-terminal.

The protected HCG [127–145] is preferably synthesized by a modified Geiger method using WSCI with condensation of the C-terminal fragment 132–145 and the N-terminal fragment 127–131. The C-terminal fragment 132–145 is preferably synthesized by condensation of fragment 132–137 and fragment 138–144 by a modified Geiger method using WSCI. The N-terminal fragment 127–131 is preferably synthesized by condensation of the fragment 127–129 and fragment 130–131 by a modified Geiger method using WSCI.

Protected HCG [118–145] is preferably synthesized by condensation of the C-terminal fragment 127–145, i.e. protected HCG [127–145] and the N-terminal fragment 118–126 by a modified Geiger method using WSCI. The C-terminal fragment 118–126 is preferably synthesized by condensation of fragment 118–121 and fragment 122–126 by the azide method.

Protected HCG [105–145] is preferably synthesized by condensation of the C-terminal fragment 112–145 and the N-terminal fragment 105–111 by a modified Geiger method using WSCI. The C-terminal fragment 112–145 is preferably synthesized by sequential condensation of protected HCG [118–145] and fragment 116–117, fragment 113–155 and the 112th amino acid by the active ester method. The N-terminal fragment 105–111 is preferably condensed by the azide method from fragment 110–111 and fragment 105–109.

Protected HCG [100–145] is preferably condensed by the active ester method with the C-terminal fragment 112–145 and the N-terminal fragment 100–111. The N-terminal fragment 100–111 is preferably condensed from the fragment 100–104 and the fragment 105–111 by the azide method.

Protected [Tyr$^{100}$]-HCG [100–145] is preferably synthesized by condensation of the C-terminal fragment 112–145 and the N-terminal fragment 100–111 by the active ester method. The N-terminal fragment 100–111 is preferably condensed from the fragment 100–104 and the fragment 105–111 by the azide method.

In the peptide synthesis hereinabove, the C-terminal carboxyl group need not always be protected. For example, in the condensation reaction by the azide or active ester method, it is not necessary to protect this group. The carboxyl group can be protected by esterification such as by formation of the methyl, ethyl or benzyl ester. The ester group such as a methyl ester can be removed with dilute sodium hydroxide solution or by conversion of the hydrazide, and the benzyl ester group can be removed with anhydrous hydrogen fluoride or by catalytic hydrogenation. The α-amino group of the peptide is protected by a conventional protective group, such as a benzyloxycarbonyl, t-butoxycarbonyl or t-amyloxycarbonyl group. The benzyloxycarbonyl group is removed by catalytic hydrogenation and the t-butoxycarbonyl and t-amyloxycarbonyl groups are removed by trifluoroacetic acid. The preferred protective groups are: the hydroxyl groups of serine and threonine by the benzyl groups; the hydroxyl group of tyrosine by a 2,6-dichlorobenzyl group; ε-amino group of lysine by an o-chlorobenzyloxycarbonyl group; the amino group in the guadinino group of arginine by a tosyl group; and the mercapto group of cysteine by a p-methoxybenzyl group. These protective groups can be removed by anhydrous hydrogen fluoride. An acetamide methyl group can be used as a protective group for the mercapto group of cysteine. Since this group is not removed by anhydrous hydrogen fluoride, it can be removed by mercuric acetate at pH 4 at the time of removal of the other groups.

Thus protected HCG [127–145], protected HCG [118–145], protected HCG [105–145], protected HCG [100–145] and protected [Tyr$^{100}$]-HCG [100–145] are obtained. Their protective groups are preferably split by acid decomposition such as one-step removal with anhydrous hydrogen fluoride to obtain the corresponding compound of the formula [I].

When the mercapto group of the 110th and/or 100th cysteine is protected by an acetamide methyl group, it can be removed with mercuric acetate at pH 4 after removal of the other protective groups with anhydrous hydrogen fluoride.

The above compound [I] can be purified by known purification methods for peptides. For example, it can be purified by column chromatography using Sephadex LH-20 (trade name), Sephadex G-50 (trade name), Dowex 1 (trade name) and carboxy methyl cellulose.

The peptide [I] can be obtained in the form of the base or its salt, preferably its salt with an organic acid such as acetic acid.

HCG can be assayed by immune reaction using antibodies obtained from peptide [I] as an antigen, or by using peptide [I] itself as an antigen, by any of the known techniques of enzyme immuno assay, radio immuno assay, a hemagglutination inhibition reaction, or a hemagglutination reaction or latex fixation test. Examples are illustrated hereinbelow.

[PREPARATION OF ANTISERUM]

EXAMPLE 1

500 μg each of HCG [118–145], HCG [110–145], [Cys(Acm)$^{110}$]-HCG [110–145], [Cys(Acm)$^{110}$]-HCG [105–145] and [Cys(Acm)$^{110}$]-HCG [100–145] were dissolved in physiological saline and mixed with equal amount of Freund's complete adjuvant to prepare an emulsion. Aliquots thereof were injected in each of 5 male guinea pigs weighing 280–350 g, the first time into the limbs and rump, and the second and subsequent times subcutaneously in the neck. Blood was collected by heat puncture on the 10th day.

The thus-obtained antibodies are designated as Lot A-2, Lot B-3, Lot C-2, Lot D-1 and Lot E-1.

EXAMPLE 2

WSCI (200 mg) was added to a solution of BSA (bovine serum albumin) (30 mg) and HCG [127–145] (60 mg) dissolved in 0.1 M phosphate buffer (pH 8.0, 1 ml) and stirred at room temperature for 30 minutes. The reaction mixture was passed through a column of Sephadex G-50 (1.5×50 cm) with distilled water for gel-filtration. The fraction containing BSA-HCG [127–145] was collected and lyophilized to obtain BSA-HCG [127–145] (34 mg).

The product (1 mg) dissolved in physiological saline (2 ml) was injected into guinea pigs as described in Example 1 and the blood was collected. The antibody obtained was designated Lot F-1.

EXAMPLE 3

BSA (60 mg) and 2,2'-dithiobenzothiazyl propionic acid (0.2 mg) were dissolved in 0.1 M phosphate buffer (pH 7.5, 2 ml) and stirred at 0° C. for 10 minutes. A solution of 2,2'-dithiobenzothiazyl propionic acid succinimide ester (6 mg) in DMF (0.3 ml) was added thereto and the mixture was stirred at 0° C. for one hour. The reaction mixture was adjusted to pH 5 by adding 1 N HCl and was passed through a column of Sephadex G-50 (1.5×50 cm) using 0.1 M phosphate buffer (pH 7.5) for gel filtration. The fractions at 27–35 ml were collected. 3.2 ml thereof (containing 20 mg of BSA) were sampled, HCG [100–145] (20 mg) was added thereto and the mixture was stirred at 0° C. for one hour. After dialysis against distilled water for one day, the dialysate was lyophilized to obtain BSA-HCG [100–145] (36 mg).

The product (1 mg) dissolved in physiological saline (2 ml) was injected in guinea pigs as in Example 1 and the blood collected. The thus-obtained antibody is designated as Lot G-1. [Diagnosis of pregnant urine by the hemagglutination inhibition test].

Diagnosis of pregnant urine was performed by the hemagglutination inhibition test according to the method described in *Acta Endocrinol.*, 35, 261 (1960).

Positive results were obtained, when pregnant urine specimens (pregnancy of 10 weeks) were diagnozed by using any of the antibodies hereinabove. Negative hemagglutination inhibitions were confirmed by diagnosis of normal urine specimens.

The abbreviations in this specification have the following meanings:

| BOC: | t-butoxycarbonyl | AOC: | t-amyloxycarbonyl |
|---|---|---|---|
| Z: | benzyloxycarbonyl | Z—Cl: | o-chlorobenzyloxycarbonyl |
| Bzl: | benzyl | Tos: | tosyl |
| Bzl—Cl$_2$: | 2,6-dichlorobenzyl | OMe: | methyl ester |
| OEt: | ethyl ester | ONP: | p-nitrophenyl ester |
| OBzl: | benzyl ester | Cys: | L—cysteine |
| OSU: | N—hydroxysuccinimide ester | Thr: | L—threonine |
| Ser: | L—serine | Acm: | acetamidemethyl |
| MBzl: | p-methoxybenzyl | Pro: | L—proline |
| Leu: | L—leucine | Asp: | L—aspartic acid |
| Arg: | L—arginine | Gly: | glycine |
| Ala: | L—alanine | Gln: | L—glutamine |
| Lys: | L—lysine | His: | L—histidine |
| Tyr: | L—tyrosine | Ile: | L—isoleucine |
| Phe: | L—phenylalanine | TEA: | triethylamine |
| TFA: | trifluoroacetic acid | DCHA: | dicyclohexylamine |
| CHA: | cyclohexylamine | DMF: | dimethylformamide |
| THF: | tetrahydrofuran | TBA: | tribenzylamine |
| NMM: | N—methylmorpholine | HOBT: | 1-hydroxybenzotriazole |
| WSCI: | N—ethyl-N'—dimethylaminopropyl-carbodiimide. | | |

The following examples illustrate the present invention. In the examples, the following carriers and developing solvents for thin layer chromatography (TLC) are used:

Carrier: Silica-gel G.
Developer:
1. Chloroform-methanol-acetic acid (95:5:3)
2. Chloroform-methanol-acetic acid (85:15:5)
3. Chloroform-methanol-acetic acid (85:10:5)
4. Chloroform-methanol-acetic acid (80:25:2)
5. Chloroform-methanol-acetic acid (24:6:1)
6. Chloroform-ethanol-ethyl acetate (5:2:5)
7. Ethyl acetate
8. Ethyl acetate-methanol (10:1)
9. Ethyl acetate-benzene (1:1)
10. Butanol-acetic acid-water (3:1:1)

Carrier: Merck cellulose.
Developer:
11. Butanol-pyridine-acetic acid-water (15:10:3:12)

EXAMPLE 4

HCG [127–145]

H-SER-LEU-PRO-SER-PRO-SER-ARG-LEU-PRO-GLY-PRO-SER-ASP-THR-PRO-ILE-LEU-PRO-GLN-OH (1) P(143–144): BOC-Leu-Pro-OBzl [1]

THF (300 ml) was added to BOC-Leu-OH.H$_2$O (149.59 g, 0.6 M). THF (150 ml) and DMF (100 ml) were added thereto to prepare a solution. Then H-Pro-OBzl (152.28 g, 0.63 M) was added thereto, and WSCI (120.8 ml, 0.66 M) was added dropwise at −10° C., and further DMF (100 ml) was added; then the mixture was stirred at room temperature overnight. After distilling off the solvent in vacuo, ethyl acetate (600 ml) was added to the residue, which was then washed three times with 5% aqueous sodium bicarbonate, twice with 1 N HCl and twice with water. The ethyl acetate layer was dried with anhydrous sodium sulfate and concentrated in vacuo. The resultant oily material was dissolved in benzene (1 l.) and concentrated in vacuo to obtain an oily substance [1].

TLC: Rf$_1$=0.89

(2) P(142–144): BOC-Ile-Leu-Pro-OBzl [2]

TFA (300 ml) was added to the substance [1] (192 mM) dissolved in methylene chloride (100 ml), and the mixture was stirred at room temperature for 30 min. TFA was distilled off in vacuo. Hexane was added thereto, and distilled off in vacuo. The oily residue dissolved in THF (200 ml) was neutralized with NMM (56.1 ml) to pH 7 with ice cooling. BOC-Ile-OH.H$_2$O (38.33 g, 159.5 mM) and HOBT (21.55 g, 159.5 mM) were added thereto. The mixture was dissolved in DMF (100 ml) and WSCI (34.1 ml) was added dropwise with ice cooling, then the mixture was stirred at room temperature overnight. Solvent was distilled off in vacuo and ethyl acetate (500 ml) was added to the residue, which was then washed three times with 5% sodium bicarbonate, once with saturated sodium chloride solution, twice with B 1 N-HCl, twice with saturated sodium chloride solution and once with water in that order. The washed solution was dried with anhydrous sodium sulfate and concentrated in vacuo. Hexane was added to the residue and the precipitate separated by decantation. Recrystallization was effected from ethyl acetate-hexane. During filtration, a small part was dissolved, and the remainder was dissolved in benzene and lyophilized to yield the substance [2] (yield: 90.9%).
m.p.: 60°–64° C.
$[\alpha]_D^{24}$: −66.34° (c=1, DMF)
TLC: $Rf_1 = 0.63$

(3) P(142-144): BOC-Ile-Leu-Pro-OH [3]

Substance [2] (76.98 g, 145 mM) was dissolved in n-butanol (20 ml) and ethanol (300 ml). 5% Pd/C (15 g) was added thereto and catalytic hydrogenation was allowed to proceed for 3 hours. After removing the catalyst, the mother liquor was concentrated in vacuo. Diethyl ether (300 ml) was added to the residue, which was then extracted successively with 500 ml and 200 ml of 5% aqueous sodium bicarbonate. The extract was adjusted to pH 4 by adding 1 N HCl with ice cooling to precipitate the product continuously, which was extracted with ethyl acetate and washed twice with water. After drying with anhydrous sodium sulfate, the solution was concentrated in vacuo. The residue was solidified by adding ether-hexane. Recrystallization was effected with ethyl acetate-ether-hexane to obtain the substance [3] (60.33 g, yield: 94.2%).
m.p.: 114°–119° C.
$[\alpha]_D^{24}$: −61.98° (c=1, DMF)
TLC: $Rf_1 = 0.53$, $Rf_6 = 0.47$

| Elemental analysis [$C_{22}H_{39}O_6N_3$]: | | |
|---|---|---|
| | C % | H % | N % |
| Found: | 59.82 | 9.42 | 9.56 |
| Calculated: | 59.84 | 8.90 | 9.52 |

(4) P(142-145): BOC-Ile-Leu-Pro-Gln-OBzl [4]

TFA (150 ml) was added to BOC-Gln-OBzl (36.41 g, 108 mM) dissolved in methylene chloride (100 ml) and the mixture was stirred at room temperature for 30 minutes. The TFA was distilled off in vacuo and the residue was dissolved in THF (100 ml) which was adjusted to pH 7 by adding FNMM (40 ml) while cooling with a freezing mixture. A solution (100 ml) of substance [3] (47.69 g, 108 mM) in THF and DMF solution of HOBT (14.50 g, 108 mM) was added thereto. WSCI (19.76 ml, 108 mM) was added dropwise while cooling with a freezing mixture during 10 minutes and the mixture was stirred overnight. Ethyl acetate (500 ml) was added to the reaction mixture, which was then washed with 5% aqueous sodium bicarbonate. The aqueous layer was extracted with ethyl acetate (300 ml). The ethyl acetate layer was combined and washed with 5% aqueous sodium bicarbonate, saturated sodium chloride, 1 N HCl (twice), saturated sodium chloride (twice) and water, in that order. The solution was dried with anhydrous sodium sulfate and concentrated in vacuo. The residue was solidified by adding ether-hexane. Recrystallization was effected from ethyl acetate (400 ml) to obtain the substance [4] (56.98 g, yield: 80.0%).
m.p.: 141°–143° C.

| Elemental analysis [$C_{34}H_{53}O_8N_5$]: | | |
|---|---|---|
| | C % | H % | N % |
| Found: | 61.76 | 8.41 | 10.84 |
| Calculated: | 61.89 | 8.10 | 10.61 |

(5) P(140-141): BOC-Thr(Bzl)-Pro-OBzl [5]

BOC-Thr(Bzl)-OH (32.88 g, 0.15 M) was dissolved in THF (100 ml). HOBT (20.94 g, 0.155 M) and H-Pro-OBzl.HCl (37.47 g, 0.155 M) were added thereto, and DMF (200 ml) was added to prepare a solution. WSCI (28.37 ml, 0.155 M) was added dropwise during 10 minutes while cooling with a freezing mixture, then the mixture was stirred at room temperature overnight. The solvent was distilled off in vacuo. Ethyl acetate (500 ml) was added to the residue, which was then washed with 5% aqueous sodium bicarbonate (twice), saturated sodium chloride solution, 1 N HCl (twice), saturated sodium chloride (twice) and water, in that order. After drying with anhydrous sodium sulfate, the solvent was distilled off and the mixture was concentrated in vacuo to obtain oil substance [5] (57.41 g, yield: 77.1%).
TLC: $Rf_6 = 0.85$, $Rf_1 = 0.03$

(6) P(140-141): BOC-Thr(Bzl)-Pro-OH [6]

Substance [5] (52.78 g, 106.29 mM) was dissolved in methanol (300 ml). 1 N NaOH (150 ml, 1.4 molar excess) was added dropwise during 20 minutes with ice cooling and then the mixture was stirred at room temperature. 1 N HCl (43.71 ml, 0.4 molar excess) was added with ice cooling to adjust to pH 7 and methanol was distilled off in vacuo. The aqueous layer was washed with ether (150 ml) and the pH of the aqueous layer was adjusted to pH 3 by adding 1 N HCl (110 ml). The solution was extracted twice with ethyl acetate (300 ml and 150 ml). The extract was dried by adding anhydrous sodium sulfate, then concentrated in vacuo. Ether and hexane were added to the residue to obtain the precipitate. The same operation was repeated and the precipitate was dissolved in ethyl acetate, then dried in vacuo to obtain the foaming solid substance [6] (32.27 g, yield: 77.75%).
m.p.: 50°–55° C.
$[\alpha]_D^{24}$: −36.64° (c=1, DMF)
TLC: $Rf_6 = 0.34$

| Elemental analysis [$C_{21}H_{30}O_5N_2.H_2O$]: | | |
|---|---|---|
| | C % | H % | N % |
| Found: | 62. | 7.62 | 6.67 |
| Calculated: | 61.75 | 7.90 | 6.86 |

(7) P(140-145): BOC-Thr(Bzl)-Pro-Ile-Leu-Pro-Gln-OBzl [7]

The substance [6] (54.77 g, 83 mM) was added to methylene chloride (80 ml). TFA (240 ml) was added with ice cooling and stirred at room temperature for 25 minutes. TFA was distilled off at 0° C. in vacuo and ether was added to the residue. The precipitate was separated by filtration and the filtered solution was concentrated in vacuo. Ether was added to the concentrate to precipitate the material. The precipitate was combined and dried in a desiccator over alkali overnight. The precipitate was dissolved in DMF (200 ml) which was adjusted to pH 7 by adding NMM (9.5 ml) while cooling with a freezing mixture. HOBT (11.21 g, 83 mM) and BOC-Thr(Bzl)-Pro-OH (32.27 g, 83 mM) and DMF (40 ml) were added thereto to prepare a solution. WSCI (15.19 ml, 83 mM) was added dropwise during 10 minutes while cooling with a freezing mixture. After 2 hours reaction, the reaction mixture was stirred at room temperature overnight. The DMF was distilled off in vacuo. 5% aqueous sodium bicarbonate (300 ml) was added to the residue which was then extracted twice with ethyl acetate (800 ml and 300 ml). The ethyl acetate layer was washed twice with 5% aqueous sodium bicarbonate, then with saturated sodium chloride solution, twice with 1 N HCl, twice with saturated sodium chloride, and with water, in that order.

The ethyl acetate layer was dried with anhydrous sodium sulfate, then concentrated in vacuo. The precipitated material was separated by adding ether. Recrystallization was effected from ethyl acetate and ether was added thereto to obtain the substance [7] (63.98 g, yield: 81.3%).

m.p.: 101°–103° C.
$[\alpha]_D^{24}$: −61.78° (c=1, DMF)

| Elemental analysis $[C_{50}H_{73}O_{11}N_7 \cdot H_2O]$: | | | |
|---|---|---|---|
| | C % | H % | N % |
| Found: | 62.21 | 7.89 | 10.03 |
| Calculated: | 62.16 | 7.82 | 10.15 |

Amino acid analysis [1.330 mg/HCl 0.3 ml, acetic acid 0.3 ml, anisole 0.1 ml, 105° C., 24 hours]: Thr 0.84 (1), Pro 2, Ile 0.97 (1), Leu 1.00 (1), Gln 0.98 (1).

(8) P(139–145):
BOC-Asp(Bzl)-Thr(Bzl)-Pro-Ile-Leu-Pro-Gln-OBzl [8]

The substance [7] (63.98 g, 67.48 mM) dissolved in methylene chloride (150 ml) was added to TFA (300 ml) with ice cooling, and then the mixture was stirred at room temperature for 30 minutes. The TFA was distilled off in vacuo at 0° C. and ether was added to the residue. The precipitate was filtered and was combined with a second batch of crystals obtained from the mother liquor, and dried over alkali in a desiccator overnight (yield: 67.1 g). The precipitate was dissolved in DMF (350 ml), which was adjusted to pH 7 by adding NMM (7.42 ml) while cooling with a freezing mixture. BOC-Asp(OBzl)-OH (29.77 g, 87.72 mM) and HOBT (11.85 g, 87.72 mM) were added thereto. WSCI (16.05 ml, 87.72 mM) was added dropwise while cooling with a freezing mixture. After 2 hours, the temperature was brought to room temperature and the mixture was then stirred overnight. The solvent was distilled off and water was added to the residue, then the precipitate formed was separated by decantation with ice cooling. The precipitate, dissolved in ethyl acetate (1.5 l.), was washed with 5% sodium bicarbonate (twice), saturated sodium chloride solution (once), 1 N HCl (once), saturated sodium chloride solution (twice) and water (once), in that order. After drying with anhydrous sodium sulfate, the mixture was concentrated in vacuo. The concentrate was allowed to stand and the precipitate formed was separated by filtration. Recrystallization was effected twice from ethyl ether to obtain the substance [8] (yield: 94.8%).

m.p.: 99°–103° C. P $[\alpha]_D^{24}$: −82.44° (c=1, DMF)
TLC: $Rf_3$=0.62, $Rf_2$=0.79

| Elemental analysis $[C_6H_{84}O_{14}N_8]$: | | | |
|---|---|---|---|
| | C % | H % | N % |
| Found: | 63.38 | 7.56 | 9.80 |
| Calculated: | 63.52 | 7.34 | 9.72 |

(9) P(138–145):
BOC-Ser(Bzl)-Asp(OBzl)-Thr(Bzl)-Pro-Ile-Leu-Pro-Gln-OBzl [9]

Methylene chloride (100 ml) was added to the substance [8] (73.88 g, 63.97 mM). TFA (300 ml) was added thereto with ice cooling and the mixture was stirred at room temperature for 30 minutes. TFA was distilled off in vacuo at 0° C. Ether was added to the residue, and the precipitate thus formed was dried over potassium hydroxide in a desiccator overnight. The precipitate, dissolved in DMF (200 ml), was adjusted to pH 7 by adding NMM (5 ml) while cooling with a freezing mixture. BOC-Ser(Bzl)-OH (24.56 g, 83.16 mM), HOBT (11.23 g, 83.16 mM) and DMF (50 ml) were added thereto. Additional WSCI (15.22 ml) was added dropwise while cooling with a freezing mixture, then more NMM (2.03 ml) was added to adjust the mixture to pH 6. After 2 hours, the temperature was brought to room temperature, and the mixture was stirred overnight. The DMF was distilled off in vacuo, and the residue was poured into cold water (2 l.). The thus-formed precipitate was collected by filtration and extracted with $CHCl_3$ (5 l.) and 5% aqueous sodium bicarbonate (2 l.). After washing the chloroform layer was 5% sodium bicarbonate, saturated sodium chloride, 1 N HCl, saturated sodium chloride and water, in that order, the organic layer was dried by adding anhydrous sodium sulfate. The solvent layer was dried in vacuo and ethyl acetate-ether-hexane was added to the residue. The precipitate formed was dissolved in chloroform (300 ml), ethyl acetate (1 l.) was added thereto, and then the chloroform was distilled off. The thus-obtained suspension was mixed with ether-hexane to obtain a precipitate. Recrystallization was repeated by the same method to obtain the substance [9] (yield: 95.1%, 80.95 g).

m.p.: 120°–122° C.
TLC: $Rf_2$=0.70

| Elemental analysis $[C_{71}H_{95}O_{16}N_9]$: | | | |
|---|---|---|---|
| | C % | H % | N % |
| Found: | 63.87 | 7.38 | 9.62 |
| Calculated: | 64.09 | 7.20 | 9.47 |

(10) P(136–137): BOC-Gly-Pro-OBzl [10]

THF (100 ml), DMF (100 ml) and HOBT (20.94 g, 0.155 M) were added to BOC-Gly-OH (26.28 g, 0.15 M). A DMF solution (20 ml) of H-Pro-OBzl.HCl (37.47 g, 0.155 M) was added thereto; the mixture was cooled to −10° C. and WSCI (28.37 ml, 0.155 M) was added dropwise during 10 minutes. After adding DMF (30 ml), the mixture was stirred at room temperature overnight. The solvent was distilled off in vacuo, ethyl acetate (500 ml) was added, and the mixture was washed twice with 5% sodium bicarbonate, saturated sodium chloride solution, twice with 1 N HCl, twice with saturated sodium chloride solution and water, in that order. The ethyl acetate layer was dried with anhydrous sodium sulfate, and the mixture was concentrated in vacuo to obtain an oily material (67 g) which was dissolved in benzene (100 ml). The solution was charged on a column (7×33 cm) of silica gel (500 g) packed with benzene, through which further benzene (300 ml) was passed. Elution was carried out with benzene-ethyl acetate (10:1→5:1→2:1→1:1) to ethyl acetate. The fractions showing $RF_1 = 0.86$ by TLC were collected and dried in vacuo to obtain the oily material [9] (46.16 g). The remaining fractions were concentrated in vacuo and charged on a column (4.5×16 cm) of silica gel (100 g) and chromatographed in the same way as above to obtain the oily material [10] (8.78 g). Total amount: 54.94 g.

TLC: $Rf_1 = 0.86$

(11) P(134–135): BOC-Leu-Pro-OH [11]

BOC-Leu-Pro-OBzl (82.76 g, 0.252 mM) was dissolved in methanol (600 ml). 1 N NaOH (327.6 ml, 1.3 molar excess) was added dropwise with ice cooling, and the mixture was stirred for one hour at room temperature. 1 N HCl (6 ml) was added to the reaction mixture with ice cooling, then the methanol was distilled off in vacuo. After washing the water layer with benzene and ethyl acetate, 1 N HCl (260 ml) was added with ice cooling to form an oily material which was extracted with ethyl acetate. The extract was washed with saturated sodium chloride solution and water and dried with anhydrous sodium sulfate. The solution was dried in vacuo and the residue was dissolved in benzene and lyophilized to obtain the substance [11] (58.57 g, yield: 70.8%).

m.p.: 63°–67° C.
$[\alpha]_D^{24}$: −66.42° (c=1, DMF)

| Elemental analysis $[C_{16}H_{28}O_5N_2]$: | | | |
|---|---|---|---|
| | C % | H % | N % |
| Found: | 58.29 | 8.87 | 8.59 |
| Calculated: | 58.52 | 8.59 | 8.53 |

(12) P(134–137): BOC-Leu-Pro-Gly-Pro-OBzl [12]:

Methylene chloride (100 ml) and TFA (200 ml) were added to the substance [10] (54.36 g, 0.15 M) and the mixture was stirred at room temperature for 25 minutes. The TFA was distilled off in vacuo and the residue was dried over potassium hydroxide in a desiccator. After dissolving in THF (100 ml) and adding triethylamine (48 ml) to adjust to pH 7 while cooling at −10° C., a THF solution (100 ml) of the substance [11] (49.26 g, 0.15 M) and HOBT (20.27 g, 0.15 M) were added thereto. More THF (50 ml) was added and WSCI (27.45 ml) was added dropwise at −10° C. during 10 minutes. After 2 hours, the temperature was brought to room temperature and the mixture was stirred overnight. The solvent was distilled off and the residue was dissolved in ethyl acetate (700 ml), then washed with 5% sodium bicarbonate solution (500 ml). The aqueous layer was extracted with ethyl acetate (300 ml) again, combined with the ethyl acetate layer, and washed with 5% aqueous sodium bicarbonate, saturated sodium chloride solution, twice with 1 N HCl, twice with saturated sodium chloride solution and water, in that order. After drying with anhydrous sodium sulfate, the material was concentrated in vacuo. Benzene was added to the residue and the mixture was concentrated in vacuo. The concentrate was charged on a column (6.5×20 cm) of silica gel (300 g) packed with benzene and eluted with benzene→benzene-ethyl acetate (3:1→2:1)→ethyl acetate. The fractions showing $RF_1 = 0.57$ were collected and dried in vacuo to obtain the substance [12] (45.73 g) which foams during solidification. The remaining fractions were collected, concentrated in vacuo and chromatographed in the same way as above to obtain the substance [12] (18 g). The remaining fractions were concentrated in vacuo, charged on a column (4.5×15 cm) of silica gel (100 g) and eluted in the same way as above to obtain the substance [12] (7.11 g). Total amount: 70.84 g (yield: 82.64%).

m.p.: 65°–69° C.
$[\alpha]_D^{24}$: −93.64° (c=1, DMF)
TLC: $Rf_1 = 0.57$, $Rf_6 = 0.54$

| Elemental analysis $[C_{30}H_{44}O_7N_4]$: | | | |
|---|---|---|---|
| | C % | H % | N % |
| Found: | 62.98 | 7.94 | 10.07 |
| Calculated: | 62.92 | 7.74 | 9.78 |

(13) P(133–137): BOC-Arg(Tos)-Leu-Pro-Gly-Pro-OBzl [13]

TFA (220 ml) was added to the substance [12] (68.72 g, 120 mM) dissolved in methylene chloride (100 ml) and the mixture was stirred at room temperature for 20 minutes. TFA was distilled off at 0° C. in vacuo, hexane was added thereto and the mixture was dried in vacuo. The residue was dried over potassium hydroxide in a desiccator, dissolved in DMF (200 ml) and adjusted to pH 6 by adding NMM (59.4 ml) at −10° C. A DMF solution (50 ml) of BOC-Arg(Tos)-OH (53 g, 123 mM) and HOBT (16.89 g, 125 mM) was added and dissolved therein and WSCI (22.86 ml, 125 mM) was added dropwise at −10° C. during 10 minutes. After 2 hours, the reaction mixture was brought to room temperature and stirred overnight. More WSCI (3.66 ml, 0.2 mM) was added at −10° C. to the reaction mixture and the mixture was stirred at room temperature for 4 hours. The DMF was distilled off in vacuo and 5% sodium bicarbonate solution (600 ml) was added to the residue. The precipitate was extracted twice with ethyl acetate (500 ml). The extract was washed with 5% sodium bicarbonate solution, saturated sodium chloride, twice with 1 N HCl, three times with saturated sodium chloride and water, in that order. The solution was dried with anhydrous sodium sulfate and concentrated in vacuo. Ether-hexane was added to the residue and the thus-precipitated material was filtered. Recrystallization was effected from ethyl acetate-ether-hexane to obtain the substance [13] (100.77 g, yield: 95.1%).

m.p.: 107°–112° C. (decomp.)
$[\alpha]_D^{24}$: −64.84° (c=1, DMF)
TLC: $Rf_1 = 0.19$ Amino acid analysis [0.709 mg/HCl 0.3 ml, acetic acid 0.3 ml, anisole 0.1 ml, 105° C., 24 hours]: Pro (2), Gly 0.95 (1), Leu 1.01 (1) and Arg 0.90 (1).

(14) P(132–137): BOC-Ser(Bzl)-Arg(Tos)-Leu-Pro-Gly-Pro-OBzl [14]

Methylene chloride (100 ml) and TFA (400 ml) were added to the substance [13] (100.77 g, 114 mM) and the mixture was stirred at room temperature for 35 minutes. The TFA was distilled off in vacuo at 0° C., ether was added to the residue, and the precipitate was filtered. The mother liquor was concentrated in vacuo to obtain a second precipitate. The precipitates were combined and dried over potassium hydroxide overnight, and then dissolved in DMF (200 ml). NMM (10 ml) was added at −10° C. thereto to adjust the mixture to pH 8; then HOBT (16.94 g, 125.4 mM) and BOC-Ser(Bzl)-OH (37.03 g, 125.4 mM) were added dropwise at pH 5. After 2 hours the reaction mixture was brought to room temperature and stirred overnight. DMF was distilled off in vacuo and the residue was poured into ice water (1.5 l.) to obtain a precipitate, which was extracted twice with ethyl acetate (1 l. and 500 ml). The ethyl acetate layer was washed with 1 N HCl, saturated sodium chloride solution, twice with 1 N NaOH, saturated sodium chloride solution and water, in that order. After drying with anhydrous sodium sulfate, the material was concentrated in vacuo. Ether was added to the residue and the precipitate was collected by filtration. Recrystallization was effected from ethyl acetate-ether, twice, to obtain the substance [14] (107.34 g, yield: 87.0%).

m.p.: 101°–105° C.

TLC: $Rf_6=0.71$, $Rf_3=0.49$

Amino acid analysis [1.818 mg/HCl 0.3 ml, acetic acid 0.3 ml, anisole 0.1 ml, 105° C., 24 hours]: Ser 0.72 (1), Arg 0.95 (1), Leu 1.03 (1), Pro (2).

(15) P(132-137):
BOC-Ser(Bzl)-Arg(Tos)-Leu-Pro-Gly-Pro-OH [15]

The substance [14] (105.44 g, 97.43 mM) was dissolved in methanol (350 ml). 1 N NaOH (125.36 ml, 1.3 molar excess) was added dropwise with ice cooling and the mixture was stirred at room temperature for 2 hours. 1 N NaOH (20 ml) was added to the reaction mixture, which was then stirred at room temperature for 1.5 hours. 1 N HCl (49 ml) was added to the reaction mixture to adjust the same to pH 6 and the methanol was distilled off in vacuo. Water was added to the aqueous layer, which was then washed with ether (100 ml). 1 N HCl (50 ml) was added dropwise with ice cooling to the aqueous layer. As the stirring became impossible due to the formation of a precipitate of viscous material, ethyl acetate (300 ml) was added and 1 N HCl (60 ml) was added dropwise to adjust the pH of the aqueous layer to pH 2. The aqueous layer was extracted with ethyl acetate (1 l. and 500 ml), and washed twice with saturated sodium chloride solution and water. After drying with anhydrous sodium sulfate, the ethyl acetate layer was concentrated in vacuo to obtain an oily material which was solidified by adding ether. Recrystallization was effected from ethyl acetate-ether to obtain the substance [15] (95.12 g, yield: 100%).

TLC: $Rf_2=0.10$, $Rf_4=0.32$

(16) P(132-145):
BOC-Ser(Bzl)-Arg(Tos)-Leu-Pro-Gly-Ser(Bzl)-Asp(OBzl)-Thr(Bzl)-Pro-Ile-Leu-Pro-Gln-OBzl [16]

The substance [9] (49.66 g, 37.32 mM) was dissolved in methylene chloride (130 ml). TFA (220 ml) was added thereto and the mixture was stirred at room temperature for 45 minutes. The reaction mixture was concentrated in vacuo and ether was added to the residue. The precipitate was collected and dried over potassium hydroxide overnight, which was then dissolved in DMF (220 ml). After adjusting to pH 7 by adding NMM (4.10 ml) at −10° C., the substance [15] (43.72 g, 44.79 mM) and HOBT (6.56 g, 48.52 mM) were added.

After these dissolved, WSCI (8.88 ml, 48.52 mM) was added dropwise at −10° C. thereto and the mixture was stirred at room temperature for 2 days. The DMF was distilled off in vacuo, and the residue was poured into ice cold water (2 l.). The precipitate was filtered, suspended in water, washed and filtered. This operation was repeated five times at pH 6, and the product was dried in a desiccator in vacuo to obtain a solid (109 g) which was dissolved in methanol, concentrated in vacuo and azeotropically distilled by adding benzene to remove remaining water. This operation was repeated three times. Recrystallization was effected from ethyl acetate-ether to obtain a material (90.09 g) which was dissolved in chloroform (270 ml) and charged on a column of silica gel (600 g) packed with chloroform, then eluted with chloroform-methanol (20:1). The fractions showing one spot upon TLC were collected and dried in vacuo to obtain the substance [15]. The remaining fractions were concentrated in vacuo and charged on a column of silica gel (220 g) and eluted the same way as above. The fractions showing one spot upon TLC were collected and dried in vacuo. The chromatographic operation above was repeated four times to obtain the substance [16] (total mount: 64.26 g, yield: 78.9%).

TLC: $Rf_3=0.40$, $Rf_2=0.60$ m.p.: 120°–125° C.

$[\alpha]_D^{24}$: −63.3° (c=1, DMF)

| | Elemental analysis: | | |
|---|---|---|---|
| | C % | H % | N % |
| Found: | 60.66 | 7.20 | 11.50 |
| Calculated: | 60.63 | 7.09 | 11.36 |

(17) P(130-131): BOC-Ser(Bzl)-Pro-OBzl [17]

THF (100 ml, H-Pro-OBzl.HCl (31.5 g, 0.13 M) and HOBT (17.5 g, 0.13 M) were added to BOC-Ser(Bzl)-OH (35.4 g, 0.12 M), and then DMF (50 ml) was added thereto to prepare a solution. WSCI (24.8 ml) was added dropwise and stirred at 0° C. for one hour and then at room temperature overnight. The solvent was distilled off in vacuo and benzene was added to the residue, which was then washed three times with 5% sodium bicarbonate solution, three times with 1 N HCl and three times with water, in that order. After drying with anhydrous sodium sulfate, the solution was dried in vacuo to obtain the substance [17] as an oil material (58 g, yield: 100%).

TLC: $Rf_1=0.68$

(18) P(127-129): BOC-Ser(Bzl)-Leu-Pro-OBzl [18]

Methylene chloride (30 ml) was added to BOC-Leu-Pro-OBzl (71.27 g, 156 mM). TFA (350 ml) was added at 0° C. thereto and the mixture was stirred at room temperature for 30 minutes. TFA was distilled off in vacuo to obtain an oily material which was dried over potassium hydroxide for three hours. The oily material was dissolved in DMF (170 ml), which was neutralized at 0° C. by adding NMM (60 ml). BOC-Ser(Bzl)-OH (46.0 g, 156 mM) and HOBT (21.1 g, 156 mM) were added thereto to prepare a solution. WSCI (28.6 ml, 156 mM) was added dropwise at 0° C. thereto, and the mixture was stirred at 0° C. for one hour and at room temperature overnight. The DMF was distilled off and ethyl acetate (500 ml) was added to the residue, which was then washed with 5% sodium bicarbonate (three times), 1 N HCl (three times) and water (three times), in that order. After drying the ethyl acetate layer with anhydrous sodium sulfate, the organic layer was concentrated in vacuo. The oily material was dissolved in a small amount of benzene which was charged on a column of silica gel (500 g) packed with benzene, then eluted with benzene (1 l.), benzene-ethyl acetate (10:1) (2 l.), benzene-ethyl acetate (5:1) (1 l.) and benzene-ethyl acetate (1:1) (2 l.), in that order. The corresponding fractions checked by TLC were collected and concentrated in vacuo. The residue was dissolved in benzene and lyophilized to obtain the substance [18] (81 g, yield: 87.0%).

TLC: $Rf_1 = 0.81$

| Elemental analysis [$C_{33}H_{45}O_7N_3$]: | | | |
|---|---|---|---|
| | C % | H % | N % |
| Found: | 66.34 | 7.81 | 6.80 |
| Calculated: | 66.53 | 7.61 | 7.05 |

(19) P(127–129): BOC-Ser(Bzl)-Leu-Pro-OH [19]

The substance [18] (81 g, 135.5 mM) was dissolved in ethanol (300 ml). 1 N NaOH (176.15 ml, 1.3 molar excess) was added dropwise at 0° C. during 30 minutes and the mixture was stirred at room temperature for three hours. The reaction mixture was neutralized by adding 1 N HCl at 0° C. and ethanol was distilled off in vacuo. Water (300 ml) was added to the aqueous layer, which was then washed twice with ether, and 1 N HCl (150 ml) was at 0° C. and the mixture was extracted with ethyl acetate (400 ml). The ethyl acetate layer was washed with water, dried with anhydrous magnesium sulfate and concentrated in vacuo. The thus-obtained oily material was dried in vacuo. The powder was reprecipitated with ether-hexane to obtain the substance [19] (65.0 g, yield: 94.5%).

m.p.: 56°–63° C.
TCL: $Rf_1 = 0.58$
$[\alpha]_D^{22}$: $-47.1°$ (c=1, DMF)

| Elemental analysis [$C_{26}H_{39}O_7N_3$]: | | | |
|---|---|---|---|
| | C % | H % | N % |
| Found: | 61.52 | 7.71 | 8.50 |
| Calculated: | 61.76 | 7.78 | 8.31 |

(20) P(127–131): BOC-Ser(Bzl)-Leu-Pro-Ser(Bzl)-Pro-OBzl [20]

Methylene chloride (30 ml) was added to the substance [17] (58 g, 0.12 M). TFA (350 ml) was added thereto at 0° C. and the mixture was stirred at room temperature for 30 minutes. The TFA was distilled off in vacuo, and the residue was dissolved in DMF (150 ml). NMM (50 ml) was added thereto at 0° C. to neutralize the same. The substance [19] (61.1 g, 0.12 M) and HOBT (16.2 g, 0.12 M) were added therein and WSCI (22 ml, 0.12 M) was added dropwise at 0° C.; then the mixture was stirred at 0° C. for one hour and at room temperature overnight. The DMF was distilled off in vacuo and ethyl ether (400 ml) was added to the residue. After washing three times with 5% sodium bicarbonate solution, three times with 1 N HCl and three times with water, in that order, and drying with anhydrous magnesium sulfate, the solution was concentrated in vacuo. The thus-obtained oily material was dissolved in a small amount of benzene and charged on a column of silica gel (500 g) packed with benzene. Elution was carried out with benzene (500 ml), benzene-ethyl acetate (10:1) (2 l.), benzene-ethyl acetate (10:1) (2 l.), benzene-ethyl acetate (3:1) (2 l.), benzene-ethyl acetate (1:1) (4 l.) and ethyl acetate (3 l.), and the corresponding fractions were collected and checked by TLC, and then dried in vacuo to obtain the substance [20] (84.07 g, yield: 80.8%).

m.p.: 58°–65° C.
TLC: $Rf_1 = 0.51$
$[\alpha]_D$: $-63.7°$ (c=1, DMF)

| Elemental analysis [$C_{48}H_{63}O_{10}N_5$]: | | | |
|---|---|---|---|
| | C % | H % | N % |
| Found: | 66.31 | 7.25 | 8.09 |
| Calculated: | 66.26 | 7.30 | 8.05 |

Amino acid analysis: Ser 1.42 (2), Pro (2), Leu 1.01 (1).

(21) P(127–131): BOC-Ser(Bzl)-Leu-Pro-Ser(Bzl)-Pro-OH [21]

The substance [20] (74.4 g, 85.4 mM) was dissolved in methanol (300 ml), and 1 N NaOH (110 ml, 1.3 molar excess) was added dropwise at 0° C., and the mixture was stirred at room temperature for three hours. After neutralizing at 0° C. by adding 1 N HCl (26 ml), the methanol was distilled off in vacuo. The aqueous layer was washed twice with ether, 1 N HCl (86 ml) was added at 0° C. and then was extracted with ethyl acetate. The ethyl acetate layer was washed twice with water, dried with anhydrous magnesium sulfate and concentrated in vacuo. Hexane was added to the residue and the thus-formed precipitate was filtered. The precipitate was dissolved in a small amount of chloroform and charged on a column of silica gel packed with chloroform. Elution was carried out with chloroform, chloroform-ethyl acetate (1:1) and chloroform-ethanol-ethyl acetate (5:1:5). The fractions corresponding to the substance as checked by TLC were collected and dried in vacuo to obtain the substance [21] (53.75 g, yield: 81%).

TLC: $Rf_1 = 0.34$
$[\alpha]_D$: $-66.4°$ (c=1, DMF)

| Elemental analysis [$C_{41}H_{57}O_{10}N_{10}$]: | | | |
|---|---|---|---|
| | C % | H % | N % |
| Found: | 63.11 | 7.66 | 8.85 |
| Calculated: | 63.14 | 7.37 | 8.98 |

Amino acid analysis [0.77 mg/6 N HCl 0.3 ml, 105° C., 20 hours]: Ser 1.84 (2), Pro 2.06 (2), Leu (1).

(22) P(127–145): BOC-Ser(Bzl)-Leu-Pro-Ser(Bzl)-Pro-Ser(Bzl)-Arg(Tos)-Leu-Pro-Gly-Pro-Ser(Bzl)-Asp(OBzl)-Thr(Bzl)-Pro-Ile-Leu-Pro-Gln-OBzl [22]

Methylene chloride was added to the substance [16] (63.66 g, 29.17 mM). TFA (260 ml) was added at 0° C. thereto and the mixture was stirred at room temperature for 40 minutes. The TFA was distilled off in vacuo and ether was added to the residue. The precipitate thus formed was filtered and dried over potassium hydroxide overnight (67.6 g), and then was dissolved in DMF (200 ml) (pH 4). NMM (4.21 ml) was added thereto to adjust the mixture to pH 7 at −10° C. HOBT (4.73 g, 35 mM), substance [21] (27.30 g, 35 mM) and DMF (100 ml) were added thereto and WSCI (6.41 ml, 35 mM) was added dropwise at −10° C., then the mixture was stirred at −10° C. for two hours and at room temperature overnight. The solvent was distilled off in vacuo and the residue was poured into ice water (1.5 l.). The thus-formed precipitate was suspended in water and filtered. This operation of suspension and filtration was repeated five times at pH 6. The precipitate was dried for two days in vacuo, dissolved in methanol and concentrated in vacuo. Benzene was added to the residue and the material was then concentrated. The benzene treatment was repeated twice. Ether was added to the concentrate and the thus-formed precipitate was filtered. The operations from methanol treatment to ether treatment hereinabove were repeated eight times to obtain the substance [22] (79.58 g, yield: 96.2%).

m.p.: 127°–130° C.
TLC: $Rf_2 = 0.61$
$[\alpha]_D^{22}$: −67.58° (c=1, DMF)

| Elemental analysis [$C_{148}H_{207}O_{36}N_{23}S$]: | | |
|---|---|---|
| | C % | H % | N % |
| Found: | 61.05 | 6.96 | 11.03 |
| Calculated: | 60.95 | 7.15 | 11.05 |

Amino acid analysis [1.893 mg/6 N HCl 0.5 ml, 105° C., 21 hours]: Asp 0.99 (1), Thr 0.96 (1), Ser 3.74 (4), Gln 1.04 (1), Pro 6.00 (6), Ile 0.95 (1), Leu 3 (3), Arg 0.94 (1), Gly 0.98 (1).

(23) HCG [127–145]

Anisole (5 ml) was added to the substance [22] (1 g, 0.34 mM). Anhydrous hydrogen fluoride (HF) (30 ml) was added thereto at 0° C. and the mixture was stirred for one hour. The HF was rapidly removed in vacuo. Ether (100 ml) and 0.1 N acetic acid (50 ml) were added to the residue and the mixture was shaken. The aqueous layer was charged on a column (3.3×18 cm) of Dowex-1 (acetate form) and eluted with 0.1 N acetic acid. The eluate and the washing solution were combined and lyophilized to obtain the crude product (660 mg). This crude product was dissolved in 8 M aqueous urea (30 ml), adjusted to pH 9 by adding aqueous ammonia, charged on a column (4.5×120 cm) of Sephadex LH-20 and eluted with 0.1 N acetic acid. The eluate was fractionated to fractions of 10 ml each, and the fractions Nos. 58–64 were collected and lyophilized to obtain the product (540 mg). The product was dissolved in 0.1 N acetic acid (30 ml), charged on a column (5×13 cm) of carboxy methyl cellulose, washed with 0.01 M ammonium acetate buffer (pH 4.5) and gradiently eluted with 0.01 M to 0.1 M of ammonium acetate buffer (pH 4.5) (each 400 ml). The eluate was fractionated to fractions of 6 ml each, and fractions Nos. 79–86 were collected and lyophilized to obtain the material (180 mg). This was dissolved in 0.1 N acetic acid, charged on a column (3×17 cm) of Sephadex LH-20 and eluted with 0.1 N acetic acid. The eluate was fractionated to fractions of 10.5 ml each, and fractions Nos. 25–30 were collected and lyophilized to obtain HCG [127–145] (136.4 mg).

m.p.: 215°–225° C.
$[\alpha]_D^{28}$: +65° (c=0.1, 0.1 N acetic acid)
TLC: $Rf_{11} = 0.71$ Amino acid analysis: Asp 1.05 (1), Thr 0.97 (1), Ser 3.44 (4), Gln 1.10 (1), Pro 6.50 (6), Gly 1.04 (1), Ile 0.89 (1), Leu 3 (3), Arg 1.02 (1).

EXAMPLE 5

HCG [118–145]

H-SER-SER-SER-SER-LYS-ALA-PRO-PRO-
PRO-SER-LEU-PRO-SER-PRO-SER-ARG-
LEU-PRO-GLY-PRO-SER-ASP-THR-PRO-
ILE-LEU-PRO-GLN-OH (1) P(125–126): BOC-Pro-Pro-OBzl [23]

THF (180 ml), H-Pro-OBzl.HCl (43.5 g, 0.18 M) and HOBT (24.3 g, 0.18 M) were added to BOC-Pro-OH (36.6 g, 0.17 M); DMF (100 ml) was added, and WSCI (33.0 ml, 0.18 M) was added dropwise at 0° C. After stirring at 0° C. for one hour and at room temperature overnight, the solvent was distilled off in vacuo. Benzene (500 ml) was added to the residue, which was washed three times with 5% sodium bicarbonate, three times with 1 N HCl and three times with water, in that order. After drying with anhydrous sodium sulfate, the solution was concentrated in vacuo to obtain the oily material [23] (74 g, yield: 100%).

Upon keeping in the refrigerator, the material partially crystallized, and was recrystallized from benzene-hexane. However almost all the oily material remained, which was used for next reaction.

m.p.: 73°–74° C.
$[\alpha]_D$: −85.7° (c=1, DMF)

| Elemental analysis [$C_{22}H_{30}O_5N_2$]: | | |
|---|---|---|
| | C % | H % | N % |
| Found: | 65.98 | 7.81 | 6.83 |
| Calculated: | 65.65 | 7.51 | 6.96 |

TLC: $Rf_9 = 0.71$ (2) P(123–124): BOC-Ala-Pro-OBzl [24]

THF (200 ml), H-Pro-OBzl.HCl (48.3 g, 0.2 M) and HOBT (27.0 g, 0.2 M) were added to BOC-Ala-OH (37.8 g, 0.2 M); DMF (100 ml) was added, and WSCI (36.6 ml, 0.2 M) was added dropwise at 0° C. After stirring at 0° C. for one hour and at room temperature overnight, the solvent was distilled off in vacuo. The residue was dissolved in ethyl acetate (500 ml), washed three times with 5% sodium bicarbonate solution, three times with 1 N HCl and three times with water, in that order, dried with anhydrous magnesium sulfate and concentrated in vacuo. The residue was dissolved in a small amount of benzene and charged on a column of silica gel (250 g) packed with benzene. Elution was carried out with benzene (1 l.), benzene-ethyl acetate (10:1) (1 l.) and benzene-ethyl acetate (1:1) (1 l.), and the corresponding fractions were collected and checked by TLC and concentrated in vacuo to obtain the oily substance [24] (75.55 g, yield: 100%).

TLC: $Rf_1 = 0.87$ (3) P(123–124): BOC-Ala-Pro-OH [25]

The substance [24] was dissolved in ethanol (200 ml). 1 N NaOH (240 ml, 1.2 molar excess) was added dropwise at 0° C. and the mixture was stirred at room temperature. After two hours, 1 N NaOH (20 ml) was added and the mixture was further stirred for 30 minutes. The reaction mixture was neutralized with 1 N HCl (60 ml) at 0° C., and the ethanol was distilled off in vacuo. After twice washing the aqueous layer with ether (100 ml), 1 N HCl (200 ml) was added thereto at 0° C. The precipitate thus formed was filtered, washed completely and dried in vacuo. Recrystallization was effected from ethyl acetate (450 ml)-hexane to crystallize the substance [25] (47.92 g, yield: 83.8%).
m.p.: 159°–160° C.
$[\alpha]_D$: −72.9° (c=1, DMF)
TLC: $Rf_1$=0.18

| Elemental analysis [$C_{13}H_{22}O_5N_2 \cdot \frac{3}{8}H_2O$]: | | | |
|---|---|---|---|
| | C % | H % | N % |
| Found: | 52.74 | 8.13 | 9.58 |
| Calculated: | 52.34 | 7.81 | 9.38 |

(4) P(123–126): BOC-Ala-Pro-Pro-Pro-OBzl [26]

Methylene chloride (30 ml) was added to the substance [23] (74 g, 0.17 M). TFA (500 g) was added thereto at 0° C. and the mixture was stirred at room temperature for 30 minutes. The TFA was removed in vacuo and the residue was dissolved in DMF (150 ml), which was neutralized by adding NMM (60 ml) at 0° C. After adding substance [25] (47.9 g, 0.16 M) and HOBT (23 g, 0.17 M), WSCI (33 ml, 0.17 M) was added at 0° C. and the mixture was stirred for one hour at 0° C. and at room temperature overnight. The DMF was distilled off in an amount of about 80 ml. Ethyl acetate (500 ml) was added to the residue which was then washed with 5% sodium bicarbonate solution, 1 N HCl and water, each three times, in that order. After drying the ethyl acetate layer with anhydrous magnesium sulfate, the solution was concentrated in vacuo. Hexane was added to the residue, and the precipitate was filtered and recrystallized twice from ethyl acetate-hexane to obtain the substance [26] (80.08 g, yield: 88.5%).
m.p.: 116°–117° C.
TLC: $Rf_2$=0.89

| Elemental analysis [$C_{30}H_{42}O_7N_4$]: | | | |
|---|---|---|---|
| | C % | H % | N % |
| Found: | 63.12 | 7.73 | 9.97 |
| Calculated: | 63.14 | 7.42 | 9.82 |

(5) P(122–126): BOC-Lys(Z-Cl)-Ala-Pro-Pro-Pro-OBzl [27]

Methylene chloride (40 ml) was added to the substance [26] (77.84 g, 136 mM), TFA (350 ml) was added at 0° C. and the mixture was stirred at room temperature for 30 minutes. The TFA was removed in vacuo and the residue was dissolved in DMF (200 ml), which was neutralized by adding NMM (80 ml) at 0° C. BOC-Lys(Z-Cl)-OH prepared from BOC-Lys(Z-Cl)-OH.TBA (80 g, 163 mM) and HOBT (220 g, 163 mM) were added thereto; WSCI (29.8 ml, 163 mM) was added dropwise, and the mixture was stirred at 0° C. for one hour and at room temperature overnight. The DMF was removed in vacuo, and ethyl acetate (600 ml) was added to the residue, which was then washed with 5% sodium bicarbonate solution, 1 N HCl and water, each three times, in that order. The ethyl acetate layer was dried with anhydrous magnesium sulfate and concentrated in vacuo. The oily material thus obtained was dissolved in the smallest amount of chloroform necessary for dissolution, and charged on a column of silica gel (500 g) packed with chloroform. Elution was carried out with chloroform (1.5 l.) and chloroform-ethyl acetate (1:1) (2 l.). The corresponding fractions as checked by TLC were collected and concentrated in vacuo to obtain the substance [27] (90.27 g, yield: 79.0%).
TLC: $Rf_6$=0.69, $Rf_2$=0.95
$[\alpha]_D$: −100.8° (c=1, DMF)

| Elemental analysis [$C_{44}H_{59}O_{16}N_6Cl \cdot H_2O$]: | | | |
|---|---|---|---|
| | C % | H % | N % |
| Found: | 59.62 | 7.07 | 9.39 |
| Calculated: | 59.68 | 6.94 | 9.49 |

Amino acid analysis: Ala 0.94 (1), Lys 0.99 (1), Pro (3).

(6) P(120–121): BOC-Ser(Bzl)-Ser(Bzl)-OMe [28]

THF (700 ml) and BOC-Ser(Bzl)-OH (23.6 g, 0.8 M) and HOBT (108 g, 0.8 M) were added to H-Ser(Bzl)-Ome.HCl (196.57 g, 0.8 M); and DMF (200 ml) was added to prepare a solution. WSCI (146 ml, 0.8 M) was added dropwise thereto at 0° C. and the mixture was stirred at 0° C. for one hour and at room temperature overnight. The reaction mixture was concentrated in vacuo, and ethyl acetate (1 l.) was added to the residue, which was then washed with 5% sodium bicarbonate solution, 1 N HCl and water, each three times, in that order. Hexane was added to the oily product, which was then crystallized by adding crystalline seed. The material was then recrystallized from ether-hexane to obtain the substance [28] (340.4 g, yield: 87.5%).
m.p.: 55°–56° C.
$[\alpha]_D$: +8.1° (c=1, DMF)
TLC: Rf=0.96

| Elemental analysis [$C_{26}H_{34}O_7N_2$]: | | | |
|---|---|---|---|
| | C % | H % | N % |
| Found: | 64.08 | 7.21 | 5.43 |
| Calculated: | 64.18 | 7.04 | 5.76 |

(7) P(118–119): BOC-Ser(Bzl)-Ser(Bzl)-NHNH$_2$ [29]

The substance [28] (191 g, 0.393 M) was dissolved in DMF (500 ml). Hydrazine hydrate (100%) (200 ml) was added dropwise and stirred at room temperature for three hours. The DMF was removed in vacuo and water was added thereto. The thus-formed precipitate was filtered, dried, and recrystallized twice from ethyl acetate-hexane to obtain the substance [29] (183.6 g, yield: 96.0%).
m.p.: 123°–124° C.
$[\alpha]_D$: +5.3° (c=1, DMF)
TLC: $Rf_9$=0.30 (substance [28] $Rf_9$=0.73)

| Elemental analysis [$C_{26}H_{34}O_7N_2$]: | | | |
|---|---|---|---|
| | C % | H % | N % |
| Found: | 64.60 | 7.34 | 5.87 |
| Calculated: | 64.18 | 7.04 | 5.76 |

(8) P(118–121): BOC-Ser(Bzl)-Ser(Bzl-Ser(Bzl)-OMe [30]

The substance [29] (146 g, 0.3 M) was dissolved in DMF (600 ml). 4.49 N HCl/dioxane solution (202 ml, 0.9 M) was added dropwise at −50° C. and isoamylnitrile (48 ml, 0.33 M) was added dropwise; then the mixture was stirred at −20° C. for 20 minutes. TEA (126 ml, 0.9 M) was added at −20° C. to obtain an azidated solution. On the other hand, to TFA at 0° C. (350 ml) was added the substance [28] (122 g, 0.25 M), and the mixture was stirred at room temperature for 30 minutes and the TEA removed in vacuo. Hexane was added to the residue, and the precipitate thus formed was filtered, dissolved in DMF (300 ml) and neutralized by adding TEA at 0° C. The neutralized solution was added to the above azide solution and stirred at 0° C. overnight. TEA.HCl was filtered and the filtrate was concentrated. To the residue was added ice and 1 N HCl, and the precipitate was collected by filtration and washed with 5% sodium bicarbonate and water. After drying in vacuo, recrystallization was carried out from methanol to obtain the substance [30] (223 g, yield: 88.4%).

$[\alpha]_D$: +9.6° (c=1, DMF)

| Elemental analysis [$C_{46}H_{56}O_{11}N_4$]: | | | |
|---|---|---|---|
| | C % | H % | N % |
| Found: | 65.81 | 6.89 | 6.73 |
| Calculated: | 65.70 | 6.71 | 6.66 |

(9) P(118-121):
BOC-Ser(Bzl)-Ser(Bzl)-Ser(Bzl)-Ser(Bzl)-NHNH$_2$ [31]

The substance [30] (98.4 g, 117 mM) was dissolved in DMF (300 ml). Hydrazine hydrate (100%) (117 ml) was added dropwise thereto and the mixture was stirred at room temperature for three hours. The DMF was distilled off in vacuo and ice water was added to the residue. The precipitate thus formed was filtered and dried. Recrystallization was effected from acetone to obtain the substance [31] (97.44 g, yield: 99%).

m.p.: 176°-177° C.
$[\alpha]_D$: +9.8° (c=1, DMF)
TLC: Rf$_7$=0.49

(10) P(118-126):
BOC-Ser(Bzl)-Ser(Bzl)-Ser(Bzl)-Ser(Bzl)-Lys(Z-cl)-Ala-Pro-Pro-Pro-OBzl) [32]

The substance [30] (60.6 g, 72 mM) was dissolved in DMF (300 ml) and 4.32 N HCl/dioxane solution (50 ml, 216 mM) was added dropwise at −50° C. After adding dropwise isoamylnitrile (11.5 ml, 80 mM) thereto, the mixture was stirred at −20° C. for 30 minutes. TEA (30 ml, 216 mM) was added at −50° C. to prepare an azide solution.

On the other hand, the substance [27] (53 g, 60 mM) was added to TEA (180 ml) at 0° C., and the mixture was stirred at room temperature for 30 minutes and the TEA was removed in vacuo. Ether was added to the residue, and the formed precipitate was filtered, dissolved in DMF (100 ml) and neutralized with NMM (15 ml) at 0° C. This neutralized solution was added to the above azide solution and stirred at 0° C. overnight. The solvent was distilled off in vacuo and ice water was added to the residue. The precipitate was collected by filtration and washed with 1 N HCl, 5% sodium bicarbonate and water. Recrystallization was effected from methanol-DMF after drying in vacuo, to obtain the substance [32], (Yield: 95.9%)

m.p.: 210°-211° C. (decomp.)
$[\alpha]_D$: −56.0° (c=1, DMF)
TLC: Rf$_6$=0.31, Rf$_1$=0.34

| Elemental analysis [$C_{84}H_{103}O_{18}N_{10}Cl.H_2O$] | | | |
|---|---|---|---|
| | C % | H % | N % |
| Found: | 63.42 | 6.72 | 8.56 |
| Calculated: | 63.28 | 6.65 | 8.78 |

Amino acid analysis: Ser 3.90 (4), Pro 3 (3), Ala 1.02 (1), Lys 1.04 (1).

(11) P(118-126):
BOC-Ser(Bzl)-Ser(Bzl)-Ser(Bzl)-Ser(Bzl)-Lys(Z-Cl)-Ala-Pro-Pro-Pro-OH [33]

The substance [32] (88.51 g, 46.2 mM) was dissolved in chloroform (600 ml), potassium hydroxide (20 g, 360 mM) in 90% methanol (500 ml) was added at 5° C., and the mixture was stirred at room temperature for four hours. The reaction mixture was neutralized by adding 1 N HCl (70 ml), the solvent was removed in vacuo, and the residue was poured into cold (5° C.) 1 N HCl (1.5 l.). The precipitate thus formed was filtered, ethyl acetate (600 ml) was added thereto and the material was washed with 1 N HCl and water (three times). The ethyl acetate layer was dried with anhydrous magnesium sulfate and concentrated in vacuo. Ether was added to the residue and the precipitate was filtered and then washed with ethyl acetate to obtain the substance [33] (55 g, yield: 80.1%).

m.p.: 125°-135° C.
$[\alpha]_D$: −56.4° (c=1, DMF)
TLC: Rf$_6$=around starting line, Rf$_5$=0.45
Amino acid analysis: Ser 3.23 (4), Pro 3 (3), Ala 0.98 (1), Lys 0.97 (1).

(12) P(118-145):
BOC-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser-(Bzl)-Arg(Tos)-Leu-Pro-Gly-Pro-Ser(Bzl)-Asp(OBzl)-Pro-Ile-Leu-Pro-Gln-OBzl [34]

Methylene chloride (200 ml) was added to the substance [22] (79 g, 28 mM) in Example 4. TFA (400 ml) was added thereto at 0° C. and the mixture was stirred at room temperature for 50 minutes. The TFA was removed in vacuo, ether was added to the residue, and the precipitate was filtered and dried over potassium hydroxide overnight in vacuo (85.35 g). This material was dissolved in DMF (270 ml, pH 3), and adjusted to pH 6 by adding NMM (4.58 ml) at −10° C. The substance [33] (49.93 g, 33.6 mM) was added and more DMF (100 ml) was added to prepare the solution. WSCI (6.20 ml) was added dropwise at −10° C. (pH 5), and then the mixture was stirred at −10° C. for two hours and at room temperature for two days. The solvent was removed in vacuo, and the residue was poured into ice cold water (1.5 l.). The precipitate formed was collected, suspended in water and repeatedly washed and dried for two days (130 g). Methanol was added thereto; the material concentrated in vacuo, and benzene was added to the residue which was then concentrated in vacuo. Recrystallization was effected by adding ether to the residue, which was preated 12 times. After adding methanol, the solution was concentrated in vacuo and recrystallized from methanol to obtain the product [34] (108.43 g, yield: 91.9%).

m.p.: 129°-131° C.
$[\alpha]_D^{24}$: −72.76° (c=1, DMF)
TLC: Rf$_2$=0.56

| Elemental analysis [$C_{220}H_{294}O_{51}N_{33}SCl$]: | | | |
|---|---|---|---|
| | C % | H % | N % |
| Found: | 61.49 | 7.07 | 11.02 |
| Calculated: | 61.67 | 6.92 | 10.79 |

Amino acid analysis [0.978 mg/6 N HCl 0.5 ml, 105° D, 21 hours]: Asp 1.00 (1), Thr 0.96 (1), Ser 6.87 (7), Gln 1.05 (1), Pro 9.63 (9), Gly 1.03 (1), Ala 1.09 (1), Ile 0.94 (1), Leu 3 (3), Lys 1.09 (1), Arg 0.97 (1).

(13) HCG [118–145]

Anisole (10 ml) was added to substance [34] (30 g, 0.71 mM). HF (80 ml) was added thereto and the mixture was stirred at 0° C. for one hour. The HF was removed in vacuo. Ether was added to the residue, and the precipitate formed was filtered. This powder, dissolved in 0.1 N acetic acid (50 ml), was charged on a column (3.5×35 cm) of Dowex-1 (acetate form) and washed with 0.1 N acetic acid. The eluate and the washing solution were combined and lyophilized to obtain the product (1.46 g), which was dissolved in 8 M urea solution (30 ml), adjusted to pH 9 by adding aqueous ammonia at 0° C., then charged on a column (4.5×120 cm) of Sephadex LH-20 and eluted with 0.1 N acetic acid. The eluate was fractionated into fractions of 7 ml each, and the fractions Nos. 55–83 were collected and then lyophilized to obtain a powder (990 mg). The powder was dissolved in 0.1 N acetic acid (30 ml) and charged on a column (5×14 cm) of CMC. After washing with 0.01 M ammonium acetate buffer (pH 4.5, 200 ml), chromatography was performed by linear gradient elution with acetate buffer (0.1 M to 0.1 M, each 400 ml, pH 4.5). Fractions Nos. 85–115 (each fraction was 6 ml) were combined, then lyophilized to obtain a powder (850 mg). The powder dissolved in 0.1 N acetic acid was charged on a column (4×120 cm) of Sephadex LH-20, and eluted with 0.1 N acetic acid. Fractions Nos. 34–43 (each fraction was 10.5 ml) were collected and lyophilized to yield a powder (650 mg). This was dissolved in 0.1 N acetic acid (30 ml) and again charged on a column (5×15 cm) of CMC, which was washed with 0.01 M ammonium acetate buffer (pH 4.5, 200 ml). Elution was carried out on a linear gradient of 0.01 M (400 ml) to 0.1 M (400 ml) ammonium acetate buffer (pH 4.5). Fractions Nos. 100–111 (each fraction was 6.5 ml) were collected and lyophilized to obtain a powder (480 mg). This powder, dissolved in 0.1 N acetic acid, was charged on a column (3×117 cm) of Sephadex LH-20 and eluted with 0.1 N acetic acid. Fractions Nos. 24–30 (each fraction was 10.5 ml) were combined and lyophilized to obtain HCG [118–145] (320 mg).

m.p.: >220° C. (decomp.)
TLC: $Rf_{11}$=0.57

Amino acid analysis: Asp 1.07 (1), Thr 0.97 (1), Ser 8.23 (8), Gln 1.13 (1), Pro 9.98 (9), Gly 1.07 (1), Ala 1.06 (1), Ile 0.89 (1), Leu 3 (3), Lys 1.08 (1), Arg. 1.07 (1).

EXAMPLE 6

[Cys(Acm)$^{110}$]-HCG [110–145]

H-Cys(Acm)-Asp-Asp-Pro-Arg-Phe-Gln-Asp-Ser-
Ser-Ser-Ser-Lys-Ala-Pro-Pro-Pro-Ser-Leu-Pro-
Ser-Pro-Ser-Arg-Leu-Pro-Gly-Pro-Ser-Asp-Thr-
Pro-Ile-Leu-Pro-Gln-OH (1) P(116–117): BOC-Gln-Asp(OBz)-OH [35]

H-Asp(OBzl)-OH (33.48 g, 150 mM) was suspended in DMF (400 ml). HOBT (2.03 g, 15 mM), BOC-Gln-ONP (55.10 g, 150 mM) and DMF (100 ml) were added thereto. The reaction mixture was adjusted to pH 7 by adding NMM (2 ml) at −10° C. and the mixture was stirred at room temperature overnight. The pH of the mixture was adjusted three times to pH 7 by adding NMM (16 ml). After the reaction (pH 6), the DMF was removed in vacuo. A citric acid solution (300 ml) and chloroform (300 ml) were added thereto and the mixture was shaken. The aqueous layer was extracted with chloroform (300 ml and 100 ml). The chloroform layers were combined and washed four times with saturated sodium chloride, acidic water (pH 3) and acidic water (pH 4), in that order. The aqueous layer was dried with anhydrous sodium sulfate and concentrated in vacuo. Ether was added to the residue and the precipitate formed was collected by filtration. Methanol was added to the collected precipitate and then the material was concentrated in vacuo, and then twice recrystallized from chloroform-ether to yield the substance [35] (32.31 g, yield: 47.7%). The mother liquor was concentrated in vacuo and recrystallized twice from chloroform-ether to obtain the substance [35] (6.3 g). Then the mother liquor was charged on a column of silica gel (100 g) and eluted with chloroform-ethanol-ethyl acetate (5:1:5). Corresponding fractions checked by TLC were dried in vacuo to obtain substance [35] (2.98 g). Total yield: 44.12 g (65.1%).

m.p.: 92°–95° C.
$[\alpha]_D^{24}$: −4.9° (c=1, DMF)
TLC: $Rf_4$=0.27, $Rf_2$=0.56

| Elemental analysis [$C_{21}H_{29}O_8N_3$]: | | | |
|---|---|---|---|
| | C % | H % | N % |
| Found: | 55.86 | 6.50 | 9.61 |
| Calculated: | 55.86 | 6.47 | 9.31 |

(2) P(116–145):
BOC-Gln-Asp(OBzl)-Ser(Bzl)-Ser(Bzl)-Ser(Bzl)-
Ser(Bzl)-Lys(Z-Cl)-Ala-Pro-Pro-Pro-Ser(Bzl)-Leu-
Pro-Ser(Bzl)-Pro-Ser(Bzl)-Arg(Tos)-Leu-Pro-Gly-Pro-
Ser(Bzl)-Asp(OBzl)-Thr(Bzl)-Pro-Ile-Leu-Pro-Gln-
OBzl [36]

The substance [34] in Example 5 (101.10 g, 24 mM) was dissolved in methylene chloride (150 ml). TFA (350 ml) was added thereto at 0° C., and the mixture was stirred at room temperature for one hour. The TFA was distilled off in vacuo, ether was added to the residue, and the precipitate thus formed was filtered and dried over potassium hydroxide overnight (114.14 g). The powder thus obtained was dissolved in DMF (300 ml) (pH 3), adjusted to pH 6 by adding NMM (8.64 ml) at 0° C., and substance [35] (13.00 g, 28.8 mM) and HOBT (3.89 g, 28.8 mM) were added to prepare a solution. PCP (7.67 g, 28.8 mM) was added thereto, along with THF (50 ml) and more DMF (50 ml). NMM (3.17 ml) was added to the solution at 0° C. (pH 5), and WSCI (5.27 ml) (pH 6) was added dropwise and the mixture was stirred at room temperature overnight. The solvent was removed in vacuo and the residue was poured into ice cold water (1.5 l.) to obtain a precipitate (pH 4), which was alternately suspended in water and washed (3 times) (pH 5). The material was then dried in vacuo, dissolved in methanol, concentrated in vacuo, and the water azeotropically distilled by adding benzene. Ether was added thereto and a precipitated viscous material was separated by decantation. More ether was added to obtain a pale brownish powder. The powder was dissolved in methanol, and benzene was added and the material was concentrated in vacuo. Ether was added to the residue to crystallize the substance. This operation was repeated seven times to yield substance [36](102.1 g, yield: 93.5%).

m.p.: 134°–139° C.
$[\alpha]_D^{24}$: −68.72° (c=1, DMF)
TLC: $Rf_2=0.40$, $Rf_4=0.93$

| Elemental analysis $[C_{236}H_{315}O_{57}N_{36}SCl.5H_2O]$: | | | |
|---|---|---|---|
| | C % | H % | N % |
| Found: | 60.87 | 6.70 | 11.00 |
| Calculated: | 61.15 | 6.85 | 10.88 |

Amino acid analysis: Asp 2.00 (2), Thr 1.03 (1), Ser 7.16 (8), Gln (2.02 (2), Pro 10.20 (9), Gly 1.09 (1), Ala 1.13 (1), Ile 0.87 (1), Leu 3 (3), Lys 1.16 (1), Arg 1.05 (1).

(3) P(114-115): AOC-Arg(Tos)-Phe-OEt [37]

AOC-Arg(Tos)-OH (63.82 g, 150 mM) was dissolved in DMF (200 ml). H-Phe-OEt.HCl (36.18 g, 157.5 mM) and HOBT (21.28 g, 157.5 mM) were added thereto. WSCI (28.82 ml, 157.5 mM) was added dropwise at −10° C. and the mixture was stirred at room temperature overnight. The DMF was removed in vacuo and a 5% sodium bicarbonate solution (500 ml) was added to the residue. The precipitate thus formed was extracted twice with ethyl acetate (500 ml-300 ml). The ethyl acetate layer was washed with 5% sodium bicarbonate, water, twice with 1 N HCl, three times with saturated sodium chloride and water, in that order. After drying with anhydrous sodium sulfate, the solution was concentrated in vacuo. Hexane was added to the residue and the precipitate was recrystallized from ethyl acetate-benzene-hexane to obtain substance [37] (85.52 g, yield: 92.3%).

m.p.: 70°–73° C.
$[\alpha]_D$: −5.12° (c=1, DMF)
TLC: $Rf_1=0.69$ (4) P(113-115): BOC-Pro-Arg(Tos)-Phe-OEt [38]

The substance [37] (85.0 g, 138 mM) was dissolved in methylene chloride (150 ml). TFA (350 ml) was added thereto at 0° C., and the mixture was stirred at room temperature for 25 minutes. The TFA was removed in vacuo and ether was added to the residue, and the precipitate was filtered and then dried over potassium hydroxide overnight. The resulting powder was dissolved in DMF (60 ml) and THF (300 ml). This solution was adjusted to pH 7 by adding NMM (15.17 ml) at −10° C. BOC-Pro-OH (29.70 g, 138 mM) and HOBT (18.64 g, 138 mM) were added thereto. WSCI (25.25 ml) was added at −10° C. thereto, and the mixture was stirred at −10° C. for two hours and at room temperature overnight. The solvent was removed in vacuo and the residue was added to 5% sodium bicarbonate (600 ml), which was then extracted twice with ethyl acetate (300 ml). The ethyl acetate layer was washed twice with 5% sodium bicarbonate, saturated sodium chloride solution, twice with 1 N HCl, three times with saturated sodium chloride solution and water, in that order, dried by adding anhydrous sodium sulfate, then concentrated in vacuo. Hexane was added to the residue, and the precipitate was collected by decantation and concentrated in vacuo after adding ethyl acetate. Hexane was added to the residue for recrystallization to obtain substance [38] (96.25 g, yield: 99.5%).

m.p.: 99°–101° C.
$[\alpha]_D^{22}$: −31.8° (c=1, DMF)
TLC: $Rf_1=0.52$, $Rf_6=0.54$

| Elemental analysis $[C_{34}H_{48}N_6S]$: | | | |
|---|---|---|---|
| | C % | H % | N % |
| Found: | 58.40 | 7.22 | 11.71 |
| Calculated: | 58.27 | 6.90 | 11.99 |

(5) P(113-115): BOC-Pro-Arg(Tos)-Phe-OH [39]

The substance [38] (35.04 g, 50 mM) was dissolved in methanol (200 ml). Ln-HCl (60 ml, 60 mM) was added dropwise during 20 minutes at 0° C. and the mixture was stirred at room temperature for 90 minutes. 1 N HCl (10 ml) was added to the reaction mixture at 0° C., methanol was removed in vacuo, and 1 N HCl (55 ml) was added thereto at 0° C. (pH 2). The precipitate was filtered and dried in vacuo (27.95 g). The filtration was extracted with chloroform. The chloroform layer was washed three times with saturated sodium chloride and water and dehydrated with anhydrous sodium sulfate, then concentrated in vacuo. The residue was combined with the above, and twice recrystallized to obtain the substance [39] (29.22 g, yield: 86.9%).

m.p.: 118°–120° C.
$[\alpha]_D^{24}$: −27.04° (c=1, DMF)
TLC: $Rf_6=0.14$, $Rf_4=0.25$ (6) P(113-145):
BOC-Pro-Arg(Tos)-Phe-Gln-Asp(OBzl)-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser(Bzl)-Arg(Tos)-Leu-Pro-Gly-Pro-Ser(Bzl)-Asp(OBzl)-Thr(Bzl)-Pro-Ile-Leu-Pro-Gln-OBzl [40]

Methylene chloride (100 ml) and TFA (350 ml) were added to substance [36] (102,01 g, 22.44 mM) and the mixture was stirred at room temperature for one hour. TFA was removed, ether added thereto, and the precipitate was filtered and dried over potassium hydroxide in vacuo overnight (120.7 g), which product was dissolved in DMF (300 ml) (pH 3). NMM (11.47 ml) was added thereto at 0° C. (pH 3). HOBT (3.94 g, 29.17 mM), a solution of PCP (7.77 g, 29.17 mM) in a mixture of DMF (50 ml) and THF (20 ml), and a DMF solution (40 ml) of substance [39] (19.63 g, 29.17 mM), were added thereto. WSCI (16.02 ml) was added dropwise (pH 3), then more NMM (5 ml), and the mixture was adjusted to pH 5 by adding NMM (5 ml) and stirred at 0° C. for two hours and at room temperature for five hours. WSCI (5.34 ml, 1.3 molar excess), (2.67 ml, 0.65 molar excess) and (2.67 ml, 0.65 molar excess), in that order, were added during two days, with continued stirring.

The solvent was removed in vacuo; the residue was poured into cold water, and the thus-precipitated material was collected by filtration. The precipitate was alternately suspended in water and filtered three times, then dried in vacuo for three days to obtain the crude product (148.49 g). The crude product was dissolved in methanol-chloroform (1:1), concentrated in vacuo, then recrystallized from ether (operations repeated ten times) to yield the product [40] (105.94 g, yield: 92.56%).

m.p.: 148°–152° C.
[α]$_D^{24}$: −67.38° (c=1, DMF)
TLC: Rf$_2$=0.42 (Merck silica gel 5715); Rf$_2$=0.58 (Merck silica gel 5721); Rf$_4$=0.89 (Merck silica gel 5715).

| Elemental analysis [C$_{263}$H$_{351}$O$_{63}$N$_{42}$S$_2$Cl.6H$_2$O]: | | | |
|---|---|---|---|
| | C % | H % | N % |
| Found: | 60.52 | 6.78 | 11.41 |
| Calculated: | 60.65 | 6.79 | 11.29 |

Amino acid analysis [5.422 mg/6 N HCl 0.5 ml, 105° C., 24 hours]: Asp 1.88 (2), Thr 0.97 (1), Ser 6.83 (8), Gln 1.93 (2), Pro 10.68 (10), Gly 1.02 (1), Ala 1.08 (1), Ile 0.94 (1), Leu 3 (3), Phe 0.75 (1), Lys 1.09 (1), Arg 1.81 (2).

(7) P(112–145):
BOC-Asp(OBzl)-Pro-Arg(Tos)-Phe-Gln-Asp(OBzl)-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser(Bzl)-Arg(Tos)-Leu-Pro-Gly-Pro-Ser(Bzl)-Asp(OBzl)-Thr(Bzl)-Pro-Ile-Leu-Pro-Gln-OBzl [41]

Methylene chloride (150 ml) and TFA (450 ml) were added to the substance [40] (104.56 g, 20.5 mM) and the mixture was stirred at room temperature for one hour. The TFA was removed in vacuo; ether was added to the residue, and the precipitate was collected by filtration and dried over potassium hydroxide overnight (125.4 g). The powder thus obtained was dissolved in DMF (300 ml) (pH 2), and the solution was adjusted to pH 7 by adding NMM (20.25 ml) at −10° C. HOBT (3.60 g, 26.65 mM), BOCZ-Asn(OBzl)-OH (8.62 g, 26.65 mM) and a THF solution (20 ml) of PCP (7.10 g, 26.65 mM) were added thereto, in that order, to prepare a solution. WSCI (8.63 ml, 47.15 mM) was added dropwise thereto (pH 7) at −10° C. and the mixture was stirred at room temperature overnight. The solvent was removed in vacuo and the residue was poured into cold water (1.5 l.). The precipitated material was filtered, suspended in water and washed, three times, and then dried in vacuo. The dried material dissolved in chloroform-methanol (1:1) was concentrated in vacuo. Recrystallization by adding ether to the residue was repeated six times to obtain the substance [41] (102.37 g, yield: 94.1%).

m.p.: 145°–150° C.
[α]$_D^{22}$; −67.6° (c=1, DMF)
TLC: Rf$_2$=0.29, Rf$_4$=0.87

| Elemental analysis [C$_{274}$H$_{366}$O$_{68}$N$_{43}$S$_2$Cl.8H$_2$O]: | | | |
|---|---|---|---|
| | C % | H % | N % |
| Found: | 60.28 | 6.69 | 11.18 |
| Calculated: | 60.39 | 6.77 | 11.05 |

Amino acid analysis [0.529 mg/6 N HCl 0.5 ml, 105° C., 24 hours]: Asp 2.63 (3), Thr 0.97 (1), Ser 6.75 (8), Gln 1.92 (2), Pro 10.65 (10), Gly 1.03 (1), Ala 1.08 (1), Ile 0.93 (1), Leu 3 (3), Phe 0.77 (1), Lys 1.09 (1), Arg 1.72 (2).

(8) P(110–111): BOC-Cys(Acm)-Asp(OBzl)-OH [42]

BOC-Cys(Acm)-OSu (77.5 g, 198 mM) was dissolved in THF (400 ml). H-Asp(OBzl)-OH (44.64 g, 200 mM) was added thereto, and the mixture was adjusted to pH 7 by adding NMM (18 ml) at 0° C.; DMF (300 ml) was added and the mixture was stirred overnight. The DMF was removed in vacuo, and 5% sodium bicarbonate (150 ml) was added to the residue, which was then washed twice with ether. The aqueous layer was adjusted to pH 3 by adding 1 N HCl (200 ml) to precipitate an oily material, which was extracted three times with ethyl acetate (300 ml), and the ethyl acetate layer was washed three times with aqueous sodium chloride and water. After drying with anhydrous sodium sulfate, the solution was concentrated in vacuo. Ether and hexane were added to the residue to obtain a precipitate. Recrystallization was effected with ethyl acetate-ether to yield the substance [42] (61.98 g, yield: 62.9%).

m.p.: 132°–134° C.
[α]$_D^{24}$: −9.76° (c=1, DMF)
TLC: Rf$_2$=0.27, Rf$_4$=0.30

| Elemental analysis [C$_{22}$H$_{31}$O$_8$N$_3$S]: | | | |
|---|---|---|---|
| | C % | H % | N % |
| Found: | 52.95 | 6.35 | 8.25 |
| Calculated: | 53.11 | 6.28 | 8.45 |

(9) P(110–145):
BOC-Cys(Acm)-Asp(OBzl)-Asp(OBzl)-Pro-Arg(Tos)-Phe-Gln-Asp(OBzl)-Ser(Bzl)-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser(Bzl)-Arg(Tos)-Leu-Pro-Gly-Pro-Ser(Bzl)-Asp(OBzl)-Thr(Bzl)-Pro-Ile-Leu-Pro-Gln-OBzl [43]

Methylene chloride (40 ml) and TFA (80 ml) were added to the substance [41] (15.92 g, 3 mM) and the mixture was stirred at room temperature for 90 minutes. The TFA was removed in vacuo, and ether was added to the residue. The precipitate was filtered and dried over potassium hydroxide (17.47 g). The resulting powder was dissolved in DMF (50 ml) (pH 3), adjusted to pH 7 by adding NMM (1.32 ml) at −10° C., the HOBT (0.53 g, 3.9 mM), a DMF solution (20 ml) of substance [42] (1.94 g, 3.9 mM), and a THF solution (20 ml) of PCP (1.04 g, 3.9 mM) were added thereto, in that order. WSCI (0.71 ml, 3.9 mM) was added dropwise at −10° C. and stirred at −10° C. for two hours and at room temperature for three hours. More WSCI (0.71 ml) was added at −10° C. thereto and stirred at room temperature overnight. The solvent was distilled off and the residue was poured into cold water (500 ml) to collect a precipitate. The precipitate was suspended in water and washed, three times, then dried in vacuo for two days (18.01 g). Chloroform-methanol (1:1) was added thereto, the mixture was concentrated in vacuo, and ether was added to the residue to crystallize the material. These operations were repeated six times to obtain the substance [43] (15.58 g, yield: 91.35%).

m.p.: 146°–148° C.
[α]$_D^{22}$: −66.72° (c=1, DMF)
TLC: Rf$_2$=0.62, Rf$_4$=0.62

| Elemental analysis [C$_{291}$H$_{391}$O$_{75}$N$_{46}$SCl.10H$_2$O]: | | | |
|---|---|---|---|
| | C % | H % | N % |
| Found: | 59.71 | 6.43 | 10.70 |
| Calculated: | 59.59 | 6.72 | 10.99 |

Amino acid analysis [0.542 mg/6 N HCl, 0.5 ml, 105° C., 22 hours]: Asp 3.38 (4), Thr 0.97 (1), Ser 6.51 (8), Gln 1.97 (2), Pro 10.00 (10), Gly 1.03 (1), Ala 1.10 (1), Ile 0.94 (1), Leu 3 (3) Phe 0.81 (1), Lys 1.11 (1), Arg 1.71 (2), Cys-Cys 0.34 (0.5).

(10) [Cys(Acm)$^{110}$]-HCG [110–145]

Anisole (20 ml) was added to the substance [43] (5.69 g, 1 mM). Anhydrous HF (100 ml) was added thereto at 0° C. and the mixture was stirred for one hour. The HF was rapidly removed in vacuo. Ether was added to the residue. The precipitate thus formed was filtered to obtain a powder (5.07 g), which was dissolved in 0.1 N acetic acid (200 ml), to which was added ether (200 ml) and the mixture was shaken. The aqueous layer was passed through a column (3×44 cm) of Dowex-1 (acetate form) and the eluate was lyophilized to obtain a powder (4.08 g). This powder was dissolved in 8 M urea solution (350 ml), adjusted to pH 9.5 by adding aqueous ammonia, and charged on a column (4.5×14 cm) of CMC. 0.01 M ammonium acetate buffer (pH 4.5, 500 ml) was passed therethrough, and the column was then eluted with a linear gradient of 0.01 M (1.5 l.) to 0.2 M (1.5 l.) ammonium acetate buffer (pH 4.5). Fractions Nos. 48–59 (each fraction was 11.8 ml) were collected and lyophilized to yield a powder (800 mg). This powder was dissolved in 0.1 N acetic acid and charged on a column (3.5×122 cm) of Sephadex LH-20, then eluted with 0.1 N acetic acid solution. Fractions Nos. 96–100 (each fraction was 64 ml) were collected and lyophilized to yield [Cys(Acm)$^{110}$]-HCG [110–145] (2.6 mg).

m.p.: >230° C. (decomp.)
$[\alpha]_D^{28}$: +81.2° (c=0.1, 0.1 N acetic acid)
TLC: Rf$_{11}$=0.43

Amino acid analysis: Asp 3.83 (4), Thr 0.95 (1), Ser 6.82 (8), Gln 2.05 (2), Pro 10.43 (10), Gly 1.10 (1), Ala 0.96 (1), Cys 0.47 (0.5), Ile 0.97 (1), Leu 3 (3), Phe 1.00 (1), Lys 1.00 (1) Arg 2.02 (2).

EXAMPLE 7

HCG [110–145]

H-CYS-ASP-ASP-PRO-ARG-PHE-GLN-ASP-
SER-SER-SER-SER-LYS-ALA-PRO-PRO-
PRO-SER-LEU-PRO-SER-PRO-SER-ARG-
LEU-PRO-GLY-PRO-SER-ASP-THR-PRO-
ILE-LEU-PRO-GLN-OH

[Cys(Acm)$^{110}$]-HCG [110–145] (50 mg) in Example 6 was dissolved in 0.1 N acetic acid (3 ml). A 0.1 N acetic acid solution (1 ml) of mercuric acetate (50 mg) was added thereto and the mixture was stirred at room temperature for four hours. 2-mercapto ethanol (1 ml) was added thereto and the mixture was stirred overnight. The solution was charged on a column (2.0×35 cm) of Sephadex G-25 and eluted with 0.1 N acetic acid. Fractions Nos. 20–30 (each fraction was 5 ml) were collected and lyophilized to obtain HCG [110–145] (47.5 mg, yield: 95%). In this sample, 51.35% mercapto groups were detected by the DTNB method.

m.p.: >240° C.
$[\alpha]_D^{28}$: +106° (c=0.1, 0.1 N acetic acid)

Amino acid analysis: Asp 3.33 (4), Thr 0.89 (1), Ser 5.65 (8), Gln 1.77 (2), Pro 9.80 (10), Gly 0.99 (1), Ala 0.99 (1), Cys-Cys 0.29 (0.5), Ile 0.98 (1), Leu 3 (3), Phe 0.98 (1), Lys 0.98 (1), Arg 1.68 (2).

Free mercapto groups: 53.15% were detected according to the method "Colorimetric assay of cysteine by Ellman method".

EXAMPLE 8

[Cys(Acm)$^{110}$]-HCG [105–145]

H-ASP-HIS-PRO-LEU-THR-CYS(ACM)-ASP-
ASP-PRO-ARG-PHE-GLN-ASP-SER-SER-
SER-SER-SER-LYS-ALA-PRO-PRO-PRO-
SER-LEU-PRO-SER-PRO-SER-ARG-LEU-
PRO-GLY-PRO-SER-ASP-THR-PRO-ILE-
LEU-PRO-GLN-OH (1) P(108–109): BOC-Leu-Thr(BzL)-OBzl [44]

H-Thr(Bzl)-OBzl.(COOH)$_2$ (68.88 g, 0.2 M) was dissolved in DMF (300 ml), the solution was neutralized by adding TEA (28 ml, 0.2 M), and HOBT (27.0 g, 0.2 M) and BOC-Leu-OH.H$_2$O (49.86 g, 0.2 M) were added thereto. WSCI (36.6 ml, 0.2 M) was added dropwise at 0° C. and the mixture was stirred at room temperature overnight. Then more WSCI (15 ml) was added and the mixture was again stirred overnight. The DMF was distilled off in vacuo and the residue was dissolved in ethyl acetate (1.2 l.). The ethyl acetate layer was washed with 5% sodium bicarbonate, water, 1 N HCl and water, in that order, dried by adding anhydrous sodium sulfate and concentrated in vacuo. The oily substance thus obtained (99.24 g, yield: 94.2%) was allowed to stand for a long time to crystallize so as to obtain the substance [44].

m.p.: 62°–64° C.
$[\alpha]_D^{21.5}$: −15.22° (c=1, DMF)
TLC: Rf$_1$=0.91, Rf$_6$=0.87

(2) P(107–109): BOC-Pro-Leu-Thr(Bzl)-OBzl [45]

Methylene chloride (150 ml) was added to the substance [44] (97.9 g, 191 mM). TFA (300 ml) and anisole (6 ml) were then added thereto at 0° C. and the mixture was stirred at room temperature for 60 minutes. The TFA was distilled off in vacuo and ether was added thereto. The resulting oily material, dissolved in DMF (600 ml), was neutralized by adding NMM at 0° C. BOC-Pro-OH (41.11 g, 191 mM) and HOBT (25.80 g, 191 mM) were added, and WSCI (35.0 ml) was added dropwise thereto at 0° C. The reaction mixture was again neutralized to pH 7 by adding NMM, then the mixture was stirred at room temperature overnight. The DMF was removed in vacuo, and the residue was dissolved in ethyl acetate (1.5 l.) which was washed with 5% sodium bicarbonate, 1 N HCl and saturated sodium chloride solution, in that other, and dehydrated with anhydrous sodium sulfate. The solution was concentrated in vacuo to obtain the oily substance [44] (111.16 g, yield: 95.4%).

TLC: Rf$_1$=0.78, Rf$_6$=0.82

(3) P(106–109): BOC-His-Pro-Leu-Thr(Bzl)-OBzl [45]

Methylene chloride (240 ml), TFA (400 ml) and anisole (8 ml) were added to the substance [44] (106.67 g, 175 mM) and the mixture was stirred at room temperature for one hour. The TFA and methylene chloride were removed in vacuo, and ether was added to the residue. The thus-precipitated material was dissolved in DMF (800 ml), adjusted to pH 7 by adding NMM, then HOBT (23.64 g, 175 m) and oily BOC-His(Tos)-OH [BOC-His(TOS-OH.DCHA (124.1 g, 210 mM) dissolved in chloroform (900 ml) and washed with 1 N nitric acid and water, dehydrated with anhydrous sodium sulfate, and concentrated in vacuo] were added thereto. WSCI (35.23 ml, 192.5 mM) was added dropwise and the mixture was stirred at room temperature overnight. The DMF was removed in vacuo, and the residue was dissolved in ethyl acetate (900 ml). The ethyl acetate solution was washed with 5% sodium bicarbonate and water, and dried with anhydrous sodium sulfate, then concentrated in vacuo to obtain an oily material. This oily material was dissolved in DMF (900 ml), HOBT (90 g) was added, and the mixture was stirred at room temperature for two days. The DMF was distilled off in vacuo and the residue was dissolved in ethyl acetate (900 ml). The solution was washed with 5% sodium bicarbonate and water, dried with anhydrous sodium sulfate, and then concentrated in vacuo. The concentrate was charged on a column (6×25 cm) of silica gel and eluted with ethyl acetate and ethyl acetate-methanol (10:1). The corresponding fractions checked by TLC were collected and dried in vacuo to obtain the powdered substance [45] (69.2 g, yield: 52.9%).

TLC: $Rf_8 = 0.35$ (4) P(106–109): BOC-His-Pro-Leu-Thr(Bzl)-NHNH$_2$ [46]

The substance [45] (67.22 g, 90 mM) was dissolved in DMF (300 ml), hydrazine hydrate (45.6 ml, 0.95 M) was added, and the mixture was stirred at room temperature overnight. The DMF was removed in vacuo and the residue was dissolved in ethyl acetate (800 ml). This solution was washed with water, dehydrated with anhydrous sodium sulfate and concentrated in vacuo to obtain the powdered substance [46] (55 g, yield: 91.1%).

(5) P(106–111): BOC-His-Pro-Leu-Thr-(Bzl)-Cys(Acm)-Asp-(OBzl)-OH [47]

TFA (180 ml) and anisole (3 ml) were added to the substance [42] (46.59 g, 93.63 mM) and the mixture was stirred at room temperature for 60 minutes. The TFA was removed in vacuo and ether was added to the residue. The precipitate was separated and dissolved in DMF (300 ml) and adjusted to pH 7 by adding TEA (26.04 ml, 187.29 mM) to obtain a de-BOC solution.

The substance [46] (52.44 g, 78.03 mM) was dissolved in DMF (300 ml). A 4.32 N HCl/dioxane solution (54.18 ml, 234.09 mM) was added thereto, then was added isoamylnitrile (11.55 ml, 85.83 mM), and then the mixture was stirred at −20° C. for 25 min. After adding TEA (32.52 ml, 234.09 mM) at −60° C., the above de-BOC solution was added thereto, and the mixture was stirred at 10° C. for three days. The DMF was removed in vacuo and the residue was dissolved in chloroform (900 ml). The solution was washed with 5% citric acid solution and water, dried with anhydrous sodium sulfate and concentrated in vacuo. The residue was charged on a column of silica-gel and eluted with chloroform-methanol (5:1). The corresponding fractions checked by TLC were collected and dried in vacuo. Recrystallization was effected from methanol-ether to obtain the substance [47] (62.79 g, yield: 77.7%).

m.p.: 117°–120° C.
$[\alpha]_D^{23}$: −24.2° (c=1, DMF)
TLC: $Rf_4 = 0.50$

| Elemental analysis [$C_{50}H_{69}O_{13}N_9S \cdot CF_3COOH$] | | | |
|---|---|---|---|
| | C % | H % | N % |
| Found: | 54.21 | 6.29 | 11.33 |
| Calculated: | 54.30 | 6.13 | 10.96 |

(6) P(105–111): BOC-Asp(OBzl)-His-Pro-Leu-Thr(Bzl)-Cys(Acm)-Asp(OBzl)-OH [48]

Methylene chloride (200 ml), TFA (300 ml) and anisole (4 ml) were added to the substance [47] (62.17 g, 60 mM) and the mixture was stirred at room temperature for 60 minutes. The TFA was removed in vacuo and ether was added to the residue. The precipitate was dissolved in DMF (500 ml), adjusted to pH 7 by adding NMM, and HOBT (8.11 g, 60 mM) and 2,4-dinitrophenol (11.05 g, 60 mM) were added thereto, then BOC-Asp(OBzl)-OSu (30.27 g, 72 mM) was added thereto at 0° C. Holding the pH at 7–8, the mixture was stirred at room temperature for two days. The DMF was distilled off, and the residue was dissolved in ethyl acetate (600 ml), washed with water and dried with anhydrous sodium sulfate. The solution was concentrated in vacuo and ether was added thereto to precipitate crystals. The precipitated crystals were purified by column chromatography, namely: silica gel (6×25 cm) eluted with chloroform-methanol (4:1); silica gel eluted with chloroform-methanol-acetic acid (80:25:2); and silica gel eluted with chloroform-methanol-acetic acid (85:15:5), in that order.

The corresponding fractions checked by TLC were collected and concentrated in vacuo to precipitate crystals by adding ether, to obtain substance [48] (65.06 g, yield: 72.8%).

m.p.: 122°–125° C.
$[\alpha]_D^{23}$: −33.22° (c=1, DMF)
TLC: $Rf_2 = 0.19$, $Rf_4 = 0.53$

| Elemental analysis [$C_{61}H_{80}O_{16}N_{10}S \cdot CF_3COOH$] | | | |
|---|---|---|---|
| | C % | H % | N % |
| Found: | 56.05 | 6.06 | 10.36 |
| Calculated: | 55.70 | 6.23 | 10.31 |

(7) P(105–145): BOC-Asp(OBzl)-His-Pro-Leu-Thr(Bzl)-Cys(Acm)-Asp(OBzl)-Asp(OBzl)-Pro-Arg(Tos)-Phe-Gln-Asp(OBzl)-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser(Bzl)-Arg(Tos)-Leu-Pro-Gly-Pro-Ser-(Bzl)-Asp(OBzl)-Thr(Bzl)-Pro-I e-Leu-Pro-Gln-OBzl [49]

Methylene chloride (50 ml) was added to the substance [41] (15.92 g, 3 mM) in Example 6, and the material was allowed to swell at room temperature for one hour. TFA (100 ml) was added and the mixture was stirred at room temperature for 1.5 hour. The TFA was removed in vacuo, and ether was added to the residue. The precipitate was dried over potassium hydroxide in vacuo overnight (17.81 g). The resulting powder was dissolved in DMF (60 ml), adjusted to pH 7 by adding NMM (1.98 ml) at −10° C., then HOBT (0.53 g, 3.9 mM), the substance [48] (4.84 g, 3.9 mM) and DMF (20 ml) were added thereto.

A THF solution (20 ml) of PCP (1.04 g, 3.9 mM) was added thereto (pH 6) and WSCI (0.71 ml, 3.9 mM) was added dropwise at −10° C. (pH 6). After stirring at −10° C. for one hour and at room temperature for two hours, more WSCI (0.71 ml, 3.9 mM) was added dropwise (pH 7) at −10° C., then the mixture was stirred at room temperature overnight. The mixture was concentrated in vacuo and the residue was poured into cold water (600 ml). The precipitate was suspended in water and filtered (this operation was repeated three times) and dried in vacuo (20.79 g). The resulting powder was dissolved in chloroform-methanol (1:1), concentrated in vacuo and the residue was dissolved in benzene, then concentrated in vacuo again to crystallize by adding ether to the residue. (This operation was repeated six times.) Gel filtration using Sephadex LH-60 column (3.5×125 cm) eluted with chloroform-methanol (1:1) was repeated three times and the eluate was concentrated in vacuo to obtain substance [49] (16.07 g, yield: 83.32%).

TLC: $Rf_4=0.86$, $Rf_2=0.55$

| Elemental analysis [$C_{330}H_{420}O_{73}N_{53}S_3Cl.8H_2O$] | | | |
|---|---|---|---|
| | C % | H % | N % |
| Found: | 60.10 | 6.48 | 11.40 |
| Calculated: | 60.30 | 6.69 | 11.29 |

Amino acid analysis: Asp 4.20 (5), Thr 1.50 (2), Ser 7.05 (8), Gln 2.04 (2), Pro 10.47 (11), Gly 1.07 (1), Ile 1.00 (1), Leu 4 (4), Phe 0.83 (1), Ala 1.14 (1), Cys-Cys 0.49 (0.5), Lys 1.16 (1), His 0.64 (1).

(8) [Cys(Acm)$^{110}$]-HCG [105–145]

Anisole (20 ml) was added to the substance [49] (6.4 g, 1 mM). Anhydrous HF (100 ml) was added thereto, and the mixture was stirred at 0° C. for one hour, then HF was rapidly removed in vacuo. Ether was added to the residue. The precipitate was dissolved in 0.1 N acetic acid (100 ml) and shaken while adding ether. The aqueous layer was passed through a Dowex-1 column (acetate form, 4.5×17 cm) and the eluate was lyophilized to obtain a powder product (4.17 g). This powder was dissolved in 8 M urea solution (250 ml), adjusted to pH 9.5 by adding aqueous ammonia and poured on a column (4.5×17.5) of CMC. The column was washed with 0.01 M ammonium acetate buffer (pH 4.5) and gradiently eluted with 0.01 M (1.5 l) to 0.1 M (1.5 l.) ammonium acetate buffer (pH 4.5). Fractions Nos. 63–73 (each fraction was 12.4 ml) were collected and lyophilized to obtain another powder material (930 mg). This latter powder was dissolved in 0.1 N acetic acid, passed through a Sephadex LH-20 column (3.5×120 cm) and eluted with 0.1 N acetic acid. Fractions Nos. 45–60 (each fraction was 6.8 ml) were collected and lyophilized to obtain another powder (770 mg). This was dissolved in water (20 ml) and poured on a column (4.5×17.4 cm) of CMC, which was washed with 0.01 M ammonium acetate buffer (pH 4.5, 500 ml). Elution was carried out with a linear gradient elution of 0.01 M (1 l.) to 0.1 M (1 l.) ammonium acetate buffer (pH 4.5). Fractions Nos. 58–77 (each fraction was 9.8 ml) were collected and lyophilized to obtain a powder (360 mg). This last powder was poured on a column (3.0×120 cm) of Sephadex LH-20 and eluted with 0.1 N acetic acid. The eluate was fractionated into aliquots each 9.3 ml in volume and the 37th to 41st fractions were collected and lyophilized to obtain a further powder (230 mg). This last powder was dissolved in 0.1 N acetic acid and poured on a column (2.5×92 cm) of Sephadex G-50 and eluted with 0.1 N acetic acid. Fractions Nos. 47 to 58 (each fraction was 5.1 ml) were collected and lyophilized to obtain [Cys(Acm)$^{110}$]-HCG [105–145] (200.1 mg).

m.p.: >230° C. (decomp.)
$[\alpha]_D^{28}$: +97.4° (c=0.1, 0.1 N acetic acid)
TLC: $Rf_{11}=0.42$ Amino acid analysis: Asp 4.44 (5), Thr 1.34 (2), Ser 5.55 (8), Gln 2.06 (2), Pro 11.76 (11), Gly 0.98 (1), Ala 1.00 (1), Cys-Cys 0.25 (0.5), Ile 0.97 (1), Leu 4 (4), Phe 1.00 (1), Lys 1.01 (1), His 1.03 (1), Arg 2.12 (2).

EXAMPLE 9

[Cys(Acm)$^{110}$]-HCG [100–145]

H-CYS-GLY-GLY-PRO-LYS-ASP-HIS-PRO-
LEU-THR-CYS(ACM)-ASP-ASP-PRO-ARG-
PHE-GLN-ASP-SER-SER-SER-SER-LYS-
ALA-PRO-PRO-PRO-SER-LEU-PRO-SER-
PRO-SER-ARG-LEU-PRO-GLY-PRO-SER-
ASP-THR-PRO-ILE-LEU-PRO-GLN-OH (1) P(100–145):
BOC-Cys(MBzl)-Gly-Gly-Pro-Lys(Z)-Asp(OBzl)-His-
Pro-Leu-Thr(Bzl)-Cys(Acm)-Asp(OBzl)-Asp(OBzl)-
Pro-Arg(Tos)-Phe-Gln-Asp(OBzl)-Ser(Bzl)-Ser(Bzl)-
Ser(Bzl)-Ser(Bzl)-Lys(Z-Cl)-Ala-Pro-Pro-Pro-
Ser(Bzl)-Leu-Pro-Ser(Bzl)-Pro-Ser(Bzl)-Arg(Tos)-
Leu-Pro-Gly-Pro-Ser(B
l)-Asp(OBzl)-Thr(Bzl)-Pro-Ile-Leu-Pro-Gln-OBzl [56]

The substance [41] (8.44 g, 1.5 mM) in Example 6 was dissolved in DMF (35 ml) (pH 3) and the solution was adjusted to pH 7 by adding NMM (0.48 ml) at −10° C. BOC-Cys(MBzl)-Gly-Gly-Pro-Lys(z)-Asp(OBzl)-His-Pro-Leu-Thr(Bzl)-Cys(Acm)-Asp(OBzl)-OH (3.78 g, 1.95 mM) and HOBT (0.26 g, 1.95 mM) were added thereto and then a THF solution (5 ml) of PCP (0.52 g, 1.95 mM) was added thereto. WSCI (0.35 ml, 1.95 mM) was added dropwise at −10° C. and the mixture was stirred at −10° C. for two hours and at room temperature for three hours. More WSCI (0.36 ml, 1.95 mM) was added dropwise in the reaction mixture at −10° C. Still more WSCI (0.11 ml, 0.6 mM) was added dropwise at −10° C. and the mixture was stirred at room temperature overnight. The DMF was removed in vacuo and the residue was added to cold water (400 ml). The precipitate was suspended and washed three times and dried in vacuo for two days. The dried material was dissolved in methanol-chloroform (1:2) and reprecipitated by adding ether, and this was repeated six times to obtain the substance [56]. (11.59 g, yield: 109.9%).

m.p.: 135°–140° C.
$[\alpha]_D^{20.5}$: −59.16° (c−1, DMF)
TLC: $Rf_2=0.21$, $Rf_4=0.80$

| Elemental analysis [$C_{359}H_{477}O_{90}N_{58}S_4Cl.10\ H_2O$] | | | |
|---|---|---|---|
| | C % | H % | N % |
| Found: | 59.58 | 6.55 | 11.53 |
| Calculated: | 59.82 | 6.67 | 11.27 |

(2) [Cys(Acm)$^{110}$]-HCG [100–145]

Thioanisole (10 ml) and L-methionine (200 mg) were added to the substance [56] (3.51 g, 0.5 mM). Anhydrous HF (70 ml) was added thereto, and the mixture was stirred at 0° C. for one hour and the HF was rapidly removed in vacuo. Ether was added to the residue and the precipitate was separated. This powder was dissolved in 0.1 N acetic acid (150 ml) and shaken with ether. The aqueous layer was passed through a column (3×40 cm) of Dowex-1 (acetate form) and the eluate was lyophilized to obtain a powder (2.79 g). This powder was dissolved in 10% mercapto ethanol in an 8 M urea solution (120 ml), adjusted to pH 9.5 by adding aqueous ammonia and the superjacent atmosphere was replaced by nitrogen gas. The mixture was then stirred for 30 minutes. The solution was poured on a column (4.5×12 cm) of CMC, which was washed with 0.1 M ammonium acetate buffer (pH 4.5). Elution was carried out by linear gradient elution of 0.01 M (1 l.) to 0.1 M (1 l.) ammonium acetate (pH 4.5). Fractions Nos. 27–35 (each fraction was 12.6 ml) were collected, lyophilized and the powder was again poured on a column (3×120 cm) of Sephadex LH-20, and eluted with 0.1 N acetic acid. Fractions Nos. 36–47 (each fraction was 6.2 ml) were collected and lyophilized to obtain a powder (400 mg). This powder was dissolved in 0.1 N acetic acid (30 ml) and poured on a column (2.5×24 cm) of CMC, which was washed with 0.01 M ammonium acetate buffer (pH 4.5). Elution was performed by linear gradient elution with 0.01 M (500 ml) to 0.1 M (500 ml) ammonium acetate buffer (pH 4.5). Fractions Nos. 61–70 (each fraction was 10.2 ml) were collected and lyophilized to obtain a powder (270 mg). This latter powder was dissolved in 0.1 N acetic acid, poured on a column (3×120 cm) of Sephadex LH-20 and eluted with 0.1 N acetic acid. Fractions Nos. 20–27 (each fraction was 9.5 ml) were collected and lyophilized to obtain a powder (160 mg). This last powder was dissolved in 0.1 N acetic acid, poured on a column (3×192 cm) of Sephadex G-50 and eluted with 0.1 N acetic acid. Fractions Nos. 55–67 (each fraction was 9 ml) were collected and lyophilized to obtain a powder (10.22 mg). 100 mg of this last powder was dissolved in 8 M urea solution (4 ml, passed through Dowex-1 column), EDTA (0.48 g) was added thereto and 3 M tris-HCl buffer (pH 8.6, 1.6 ml) and 2-mercapto ethanol (0.1 ml) were also added thereto, then the mixture was stirred at room temperature for 24 hours under nitrogen gas atmosphere. After adjusting to pH 5 by adding acetic acid, the solution was poured on a column (2.5×34 cm) of Sephadex G-25 and eluted with 0.1 N acetic acid. Fractions Nos. 8–12 (each fraction was 6 ml) were collected and lyophilized to obtain the product (92 mg). 35% free mercapto ethanol groups were detected by the DTNB method for mercapto group detection.

m.p.: >220° C. (decomp.)
$[\alpha]_D^{28}$: +127° (c=0.1, 0.1 N acetic acid)
TLC: $Rf_{11}$=0.49

Amino acid analysis: Asp 4.50 (5), Thr 1.29 (2), Ser 5.43 (8), Gln 2.06 (2), Pro 12.78 (12), Gly 2.80 (3), Ala 0.95 (1), Cys-Cys 0.34 (0.5), Ile 0.96 (1), Leu 4 (4), Phe 0.96 (1), Lys 2.06 (2), His 1.07 (1), Arg 2.02 (2).

EXAMPLE 10

[Tyr$^{100}$, Cys(Acm)$^{110}$]-HCG [100–145]

H-TYR-GLY-GLY-PRO-LYS-ASP-HIS-PRO-LEU-THR-CYS(ACM)-ASP-ASP-PRO-ARG-PHE-GLN-ASP-SER-SER-SER-SER-LYS-ALA-PRO-PRO-PRO-SER-LEU-PRO-SER-PRO-SER-ARG-LEU-PRO-GLY-PRO-SER-ASP-THR-PRO-ILE-LEU-PRO-GLN-OH
P(100–104);
BOC-Tyr(Bzl-Cl$_2$)-Gly-Gly-Pro-Lys(Z)-OBzl [57]

(1) P(100–145):
BOC-Tyr(Bzl-Cl$_2$)-Gly-Gly-Lys(Z)-Asp(OBzl)-His-Pro-Leu-Thr(Bzl)-Cys(Acm)-Asp(OBzl)-Asp(OBzl)-Pro-Arg(Tos)-Phe-Gln-Asp(OBzl)-Ser(Bzl)-Ser(Bzl)-Ser(Bzl)-Ser(Bzl)-Lys(Z-Cl)-Ala-Pro-Pro-Pro-Ser(Bzl)-Leu-Pro-Ser(Bzl)-Pro-Ser(Bzl)-Arg(Tos)-Leu-Pro-Gly-Pro-Ser(Bzl)-Asp(OBzl)-Th(Bzl)-Pro-Ile-Leu-Pro-Gln-OBzl [60]

Substance [41] (8.44 g, 1.5 mM) in Example 6 was dissolved in DMF (35 ml) (pH 3) and adjusted to pH 7 by adding NMM (0.48 ml) at −10° C. HOBT (0.26 g, 1.95 mM) and BOC-Tyr(Bzl-Cl$_2$)-Gly-Gly-Pro-Lys(Z)-Asp(OBzl)-His-Pro-Ley-Thr(Bzl)-Cys(Acm)-Asp(OBzl)-OH (3.97 g, 1.95 mM) were added, then a THF solution (5 ml) of PCP (0.52 g, 1.95 mM) was added thereto. WSCI (0.36 ml, 1.95 mM) was added dropwise at −10° C., and the mixture was stirred at −10° C. for two hours and at room temperature for three hours. More WSCI (0.36 ml, 1.95 mM) was added dropwise at −10° C. to the reaction mixture, which was stirred at room temperature overnight. Still more WSCI (0.11 ml, 0.6 mM) was added dropwise thereto at −10° C. and the mixture was stirred at room temperature overnight. The DMF was removed in vacuo, and the residue was poured into cold water (400 ml). The operations of suspending the precipitate in water and filtering were repeated three times, and then the material was dried in vacuo for two days. This dried material was dissolved in chloroform-methanol (2:1) and reprecipitated with ether. This operation was repeated six times to obtain the substance [60] (12.03 g).

m.p.: 139°–144° C.
$[\alpha]_D^{20.5}$: −55.22° (c=1, DMF)
TLC: $Rf_2$=0.18, $Rf_4$=0.89

| Elemental analysis [C$_{364}$H$_{477}$O$_{90}$N$_{58}$S$_3$Cl.10H$_2$O] | | |
|---|---|---|
| C % | H % | N % |
| Found: 59.60 | 6.47 | 11.16 |
| Calculated: 59.83 | 6.58 | 11.12 |

(2) [Tyr$^{100}$, Cys(Acm)$^{110}$]-HCG [100–145]

Anisole (15 ml) was added to the substance [60] (3.56 g, 0.5 mM). Anhydrous HF (70 ml) was added thereto, and the mixture was stirred at 0° C. for one hour and the HF was removed rapidly in vacuo. Ether was added to the residue. The precipitated white powder dissolved in 0.1 N acetic acid (200 ml) was passed through a column (4.5×16 cm) of Dowex-1 (acetate form) and the eluate was lyophilized to obtain a powder (2.42 g). More of the substance [60] (3.56 g) was treated the same way as above to obtain the same powder (2.38 g). The combined powder (4.80 g) was dissolved in 8 M urea solution (250 ml), adjusted to pH 9 by adding aqueous ammonia, and was poured on a column (3.5×17 cm) of CMC. The column was washed with 0.01 M ammonium acetate buffer (pH 4.5, 500 ml) and linear gradient elution was performed with 0.01 M (1.2 l) to 0.1 M (1.2 l.) ammonium acetate buffer (pH 4.5). Fractions Nos. 52–60 (each fraction was 12 ml) were collected and lyophilized to obtain a powder (1.72 g). This latter powder was dissolved in 0.1 N acetic acid and poured on a column (3.5×120 cm) of Sephadex LH-20 and eluted with 0.1 N acetic acid. Fractions Nos. 25–31 (each fraction was 12.4 ml) were collected and lyophilized to obtain a powder (0.63 g). This last powder was dissolved in 0.05 N acetic acid (20 ml) and poured on a column (2×32 cm) of CMC. The column was washed with 0.01 M ammonium acetate buffer (pH 4.5, 200 ml). Linear gradient elution was carried out with 0.01 M (1 l.) to 0.05 M (1 l.) ammonium acetate buffer (pH 4.5). Fractions Nos. 89–96 (each fraction was 9.4 ml) were collected and lyophilized to obtain a lyophilizate (350 mg). This lyophilizate was dissolved in 0.1 N acetic acid, poured on a column (3.5×120 cm) of Sephadex LH-20 and eluted with 0.1 N acetic acid. Fractions Nos. 24–29 (each fraction was 12.4 ml) were collected and lyophilized to obtain another lyophilizate (180 mg). This latter lyophilizate was dissolved in 0.1 N acetic acid, poured on a column (2×74 cm) of Sephadex G-50 and eluted with 0.1 N acetic acid. Fractions Nos. 18–23 (each fraction was 6 ml) were collected and lyophilized to obtain [Tyr$^{100}$, Cys(Acm)$^{110}$]-HCG [100–145] (141.1 mg).

m.p.: >235° C. (decomp.)

$[\alpha]_D^{28}$: −25° (c=0.1, 0.1 N acetic acid)

TLC: $Rf_{11}$=0.45

Amino acid analysis (under conditions of protected peptide decomposition): Asp (4.96 (5)), Thr 1.15 (2), Ser 6.26 (8), Gln 2.04 (2), Pro 12.14 (12), Gly 2.93 (3), Ala 0.93 (1), Cys-Cys 0.45 (0.5), Ile 0.93 (1), Leu 4 (4), Tyr 0.99 (1), Phe 1.00 (1), Lys 1.98 (2), His 0.97 (1), Arg 2.05 (2).

What is claimed is:

1. A peptide of the formula

R-SER-LEU-PRO-SER-PRO-SER-ARG-LEU-PRO-GLY-PRO-SER-ASP-THR-PRO-ILE-LEU-PRO-GLN-OH wherein R: H or $R_1$-Ser-Ser-Ser-Ser-Lys-Ala-Pro-Pro-Pro group, $R_1$: H or $R_2$-$R_3$-Asp-Asp-Pro-Arg-Phe-Gln-Asp group, $R_2$: H or $R_4$-Asp-His-Pro-Leu-Thr group, $R_4$: H-$R_5$-Gly-Gly-Pro-Lys group, $R_5$: Cys or Tyr group, and $R_3$: Cys or S-acetamidemethyl-Cys group, or pharmaceutically acceptable salt thereof.

* * * * *